(12) United States Patent
Hodge

(10) Patent No.: US 11,361,847 B1
(45) Date of Patent: Jun. 14, 2022

(54) SYSTEM AND METHOD FOR RAPIDLY REPORTING TESTING RESULTS

(71) Applicant: Timothy A. Hodge, Eads, TN (US)

(72) Inventor: Timothy A. Hodge, Eads, TN (US)

(*) Notice: Subject to any disclaimer, the term of this patent is extended or adjusted under 35 U.S.C. 154(b) by 0 days.

(21) Appl. No.: 17/180,823

(22) Filed: Feb. 21, 2021

Related U.S. Application Data

(60) Provisional application No. 63/146,612, filed on Feb. 6, 2021.

(51) Int. Cl.
| | | |
|---|---|---|
| *G16H 10/40* | (2018.01) | |
| *G16H 10/60* | (2018.01) | |
| *G16B 30/10* | (2019.01) | |
| *G16B 30/00* | (2019.01) | |
| *G16B 99/00* | (2019.01) | |

(52) U.S. Cl.
CPC .......... *G16H 10/40* (2018.01); *G16B 30/00* (2019.02); *G16B 30/10* (2019.02); *G16B 99/00* (2019.02); *G16H 10/60* (2018.01)

(58) Field of Classification Search
CPC ........ G16H 10/60; G16H 10/40; G16B 30/10; G16B 99/00; G16B 30/00
See application file for complete search history.

(56) References Cited

U.S. PATENT DOCUMENTS

| | | |
|---|---|---|
| 7,267,942 B2 | 9/2007 | Peiris et al. |
| 7,547,512 B2 | 6/2009 | Peiris et al. |
| 8,008,046 B2 | 8/2011 | Maltezos et al. |
| 9,460,268 B2 | 10/2016 | Holmes et al. |
| 10,055,502 B2 | 8/2018 | Li et al. |
| 10,281,367 B1 | 5/2019 | Schindler, III |
| 10,689,692 B2 | 6/2020 | Koehler et al. |
| 10,859,574 B2 | 12/2020 | Oved et al. |
| 2005/0221370 A1 | 10/2005 | Hodge |
| 2005/0239125 A1 | 10/2005 | Hodge |
| 2005/0266494 A1 | 12/2005 | Hodge |
| 2005/0272085 A1 | 12/2005 | Hodge |
| 2006/0014186 A1 | 1/2006 | Hodge et al. |
| 2006/0014192 A1 | 1/2006 | Hodge |
| 2007/0190568 A1 | 8/2007 | Hodge |
| 2007/0196853 A1 | 8/2007 | Hodge |
| 2009/0275038 A1 | 11/2009 | Hodge |
| 2010/0105050 A1 | 4/2010 | Hodge et al. |
| 2016/0245810 A1 | 8/2016 | Patel et al. |
| 2017/0032268 A1 | 2/2017 | Rajagopalan et al. |
| 2018/0230521 A1 | 8/2018 | Ecker et al. |
| 2019/0237156 A1 | 8/2019 | Eden et al. |
| 2021/0180110 A1* | 6/2021 | Shachar ............. G01N 21/6428 |

FOREIGN PATENT DOCUMENTS

| | | |
|---|---|---|
| CN | 1455003 A | 11/2003 |
| CN | 1258603 C | 6/2006 |
| KR | 20050118738 A | 12/2005 |
| RU | 2504585 C1 | 1/2014 |
| RU | 2731390 C1 | 9/2020 |

* cited by examiner

*Primary Examiner* — Jerry Lin
(74) *Attorney, Agent, or Firm* — Veritay Group IP PLLC; Susan B. Fentress; Liam O'Donnell

(57) ABSTRACT

The invention is directed to a method and system to rapidly provide a clinical reportable result for the presence of a target nucleic acid sequence in a sample. The inventive subject matter includes: a method to conduct a rapid assay to provide a clinically reportable result for the presence of a target nucleic acid sequence in a sample. A clinically reportable results is one that is automatically validated. Here the testing and quality control steps are automated to avoid delay caused by human review and validation of each assay.

11 Claims, 6 Drawing Sheets

FIG. 3

SYSTEM AND METHOD FOR RAPIDLY REPORTING TESTING RESULTS

CROSS-REFERENCE TO RELATED APPLICATIONS

None.

STATEMENT REGARDING FEDERALLY SPONSORED RESEARCH OR DEVELOPMENT

None NAMES OF PARTIES TO A JOINT RESEARCH AGREEMENT:
None

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

None

STATEMENT REGARDING PRIOR DISCLOSURE BY THE INVENTOR OR A JOINT INVENTOR

None

FIELD OF THE INVENTION

This invention relates generally to the collection of a biological sample and the management of the chain of title in compliance with HIPAA. More particularly, it relates to a process for testing biological specimens for the SARS CoV-2 virus. Further this invention relates to the ordering biological sample testing over a network such as the Internet. Even more particularly, it relates to a web-based apparatus and method for gathering information regarding an order and placing the order over the Internet.

BACKGROUND OF THE INVENTION

Traditionally, testing specimens for clinical purposes occurred in institutions such as hospitals, academical laboratories, commercial laboratories, and the like, utilizing instrumentation and chemistries approved by the FDA for clinical purposes. Clinical laboratory personnel take sample the biological materials which include swab samples (cells), saliva/sputum, tissue (including blood), cerebral spinal fluid (CSF), fecal, urine, and the like. Licensed lab staff perform the appropriate tests upon the samples in order to determine their characteristics.

In recent times, with the SARS-CoV-2 pandemic this traditional model has broken down. With the shortages of automated test equipment and reagents, with the increasing complexity of the test to be performed, and with the increasing accuracy required of any test results, and the requirements of FDA Emergency Use Authorization (EUA) it is more and more difficult for traditional hospital laboratories to perform tests quickly and in a cost-effective manner.

Genotyping biological samples is one particular area in which it is particularly beneficial to perform accurate and precise tests quickly and in a cost-effective manner. This is true primarily because genotyping is informative for clinical as well as public health purposes.

"Genotyping" refers to the process of determining the genetic constitution from nucleic acid (i.e., RNA and/or DNA) whose source is prokaryotic or eukaryotic including viral, bacterial, plant, animal or human. In current clinical laboratory testing for SARS CoV-2, much of the biological testing targets particular genetic characteristics—i.e., particular genetic sequences in the viral genome. It is these genetic characteristics, such as the presence or absence of the particular genetic sequences that both indicate the binary presence/absence of the virus, but also the subtype(s) of the virus that confer different phenotypic characteristics. The viral subtypes phenotypic differences characteristics includes increased infectivity, resistance to treatment strategics and the like. Genotyping as it is described herein refers to the process of testing viral, bacterial, fungal, plant, animal, or human materials for the existence of particular genetic sequences that define the presence or absence of a particular genetic sequences. Often the genetic sequences presence or absence may indicate a pathogen, a pathogen subtype, or mutational of endogenous sequences. In the process described below, primer, probes and/or indexes are created that are complementary to the genetic sequences that target specific genetic sequences. These primers, probes and/or indexes are placed in contact with the biological samples, typically in solution. If the genetic sequences are present in the biological samples, the primer, probes and/or indexes identify their corresponding genetic and are the to be "positive. If the genetic sequences are not present in the biological samples, the primer, probes and/or indexes do not identify their corresponding genetic sequences and the sample is the to be "negative". In another form of genotyping, the testing involves determining whether a viral, bacterial fungal, plant, animal, or human has a particular genetic "profile" that is defined by one or more primer sets, probes and or index sets.

Individual's genetic profiles are informative for a number of clinical applications. Examples include determining viral subtypes and the propensity for different cancer to be identified and treated based on the individual's genetic code. Biological researchers and physicians engage themselves in determining what treatment methodologies are effective for these diseases. Their pursuits often involve identifying actionable genetics targets in an individual's or tumors genetic code and then treating those individuals with various anti-carcinogenic materials, radiation, or chemical therapies to mitigate and potentially cures these cancers.

While it is certainly possible for individual clinicians and hospitals to perform these tests, it often requires a specialized skill set. The equipment needed is expensive. Furthermore, due to its cost, and market availability, some equipment is not generally available at hospital labs. In addition, clinical personnel that are experienced in treating cancer may not be experienced in performing the genotyping necessary to screen individual's specimens for pathogens and/or cancer characterization, susceptibility and/or treatment plans based on the genetic sequences. Performing the tests manually requires constant practice to do it accurately and quickly which is not a trivial problem. Since the primary focus of a clinician's or hospital's work is not genotyping, but patient care, the researchers may not have the necessary experience performing the tests to ensure accurate results each time. At present results for a Covid-19 test are serval days (most labs require 72 hours or more) while it is critical to reduce the time to provide a result to reduce the spread of disease.

Processes have been developed for genotyping biological samples. A serious drawback with these processes is the need to ensure the reliability of test results and to perform the tests inexpensively. To do this, automated systems and methods for processing the samples, gathering data regarding the biomedical (genotyping) tests to be conducted and for ordering those tests are required. Automation provides for faster and more accurate sample processing, entry of order information, more reliable conveyance of order information to the testing laboratory, and greater ease-of-use by individuals ordering testing. This improved system of ordering biological tests (and particularly genotyping) is described and claimed herein.

SUMMARY OF THE INVENTION

The inventive subject matter includes: a method to conduct a rapid assay to provide a clinically reportable result for the presence of a target nucleic acid sequence in a sample. A clinically reportable results is one that is automatically validated.

Here the testing and quality control steps are automated to avoid delay caused by human review and validation of each assay. A rapid result means a reportable result in around in as little as 3.5 hours but with an average of 4.8 hours.

The inventive subject matter includes: a computer implemented system to provide a reportable result to a user for the presence of a target nucleic acid sequence. This system includes: a plurality of samples, wherein each sample of the plurality of samples is disposed in a sample well, each sample well provided with a portion of the sample and a plurality of primers for amplifying the target nucleic acid sequence; an automated laboratory instrumentation configured to perform respective functions, wherein said respective functions include: obtaining a fluorescent intensity value for a polymerase chain reaction amplification cycle from each sample well; an electronic interface configured to transmit a plurality of patient specific information associated with each sample from the remote client to a LIMS computer, said LIMS computer comprised of a computer system having a microprocessor and a non-transitory computer-readable storage medium coupled to said microprocessor, wherein said non-transitory computer-readable storage medium is encoded with computer-readable instructions; wherein when said computer-readable instructions are executed, said microprocessor performs the respective functions, wherein said functions comprises: electronically generating a fluorescent intensity value range based on the fluorescent intensity value for the polymerase chain reaction amplification cycle for each sample wells for the sample and for a control; comparing, by the one or more processors, the plurality of sample fluorescent intensity values against the fluorescent intensity value range; evaluating a sample cycle threshold value for each well of the plurality of sample wells against an established cycle threshold range;
determining a positive result and a negative result for the presence of a target nucleic acid sequence in the sample by comparing the sample cycle threshold value to an established cycle threshold range; and comparing, by the one or more processors, the positive result, and the negative result for the target nucleic acid sequence against a known interpretation result set to provide a reportable result, wherein the electronic interface is configured to transmit the reportable result to the remote client.

Another aspect of the novel subject matter includes: a non-transitory computer-readable memory medium, on which computer-executable instructions are stored which, when executed on a data-processing system, prompt the data-processing system to carry out the steps of a method, of validating a plurality of fluorescent intensity values for a polymerase chain reaction amplification cycle from each of a plurality of wells for a sample and for a control. This validation method includes: electronically generating a dynamic value range based on the plurality of fluorescent intensity values for a sample and for a control; electronically generating a static value range based on the plurality of fluorescent intensity values for the sample and for the control; comparing, by the one or more processors, the plurality of sample fluorescent intensity values against the dynamic value range and the static value range; evaluating a sample cycle threshold value for each well of the plurality of sample wells against an established cycle threshold range; determining by the one or more processors, a positive result for the presence of a target nucleic acid sequence in the sample by comparing the sample cycle threshold value to an established cycle threshold range, if less than the established cycle threshold range then the sample is determined to be a positive result for the presence of the target nucleic acid sequence in the sample; determining by the one or more processors, a negative result for the presence of the target nucleic acid sequence in the sample by comparing the sample cycle threshold value to an established cycle threshold range, if greater than the established cycle threshold range then the sample is determined to be a negative result for the presence of the target nucleic acid sequence in the sample; matching by the one or more processors, the positive result and the negative result to a and known control negative results; and comparing, by the one or more processors, the positive result, and the negative result for the target nucleic acid sequence against a known interpretation result set to provide a validated test result.

Another aspect of the novel subject matter includes a method for conferring an electronic chain of custody for each sample of a plurality of samples. The method includes the steps of: receiving, by one or more processors, electronic information, over a network, associated with the sample by a laboratory LIMS 106, wherein the sample specific electronic information is comprised of a target nucleic acid sequence and patient information data; receiving a sample container for each sample of a plurality of samples, wherein a physical label is attached to the sample container, the readable physical label includes sample specific data; the physical label is comprised of a machine-readable code; tracking the sample electronically on the laboratory instrumentation by scanning the machine-readable code, providing a plurality of laboratory instrumentation configured to detect electronic fluorescent intensity data for each sample of a plurality of sample; one or more processors, applying a plurality of fluorescent intensity value ranges and a plurality of cycle threshold ranges to fluorescent intensity data for each sample of a plurality of samples to provide a reportable result for each of the sample of the plurality of samples; and electronically transmitting the reportable result electronically to the remote user.

Numerous other features and advantages of the present invention will become readily apparent from the following detailed description, the accompanying drawings, and the appending claims, in which the like items have the same item numbers.

BRIEF DESCRIPTION OF THE SEVERAL VIEWS OF THE DRAWINGS

FIG. 3 shows an exemplary data input screen of the present invention.

DETAILED DESCRIPTION OF THE INVENTION

Figure 1:
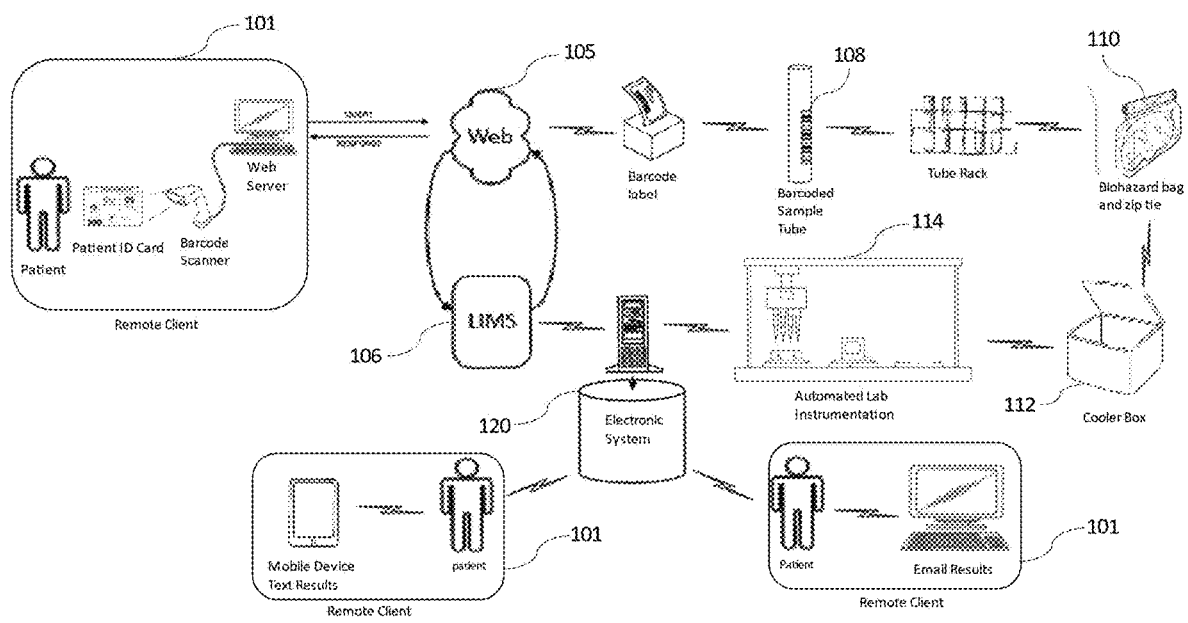
FIG. 1 shows the system of the present invention.

The present invention may be understood more readily by reference to the following detailed description of the invention. It is to be understood that this invention is not limited to the specific devices, methods, conditions, or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of an embodiments of the inventions and are not restrictive of the invention as claimed. Unless defined otherwise, all technical and scientific terms used herein have the same meaning as commonly understood by one of ordinary skill in the art to which this invention belongs.

"Entity" as used herein refers to a natural person, a partnership, a corporation, a limited liability corporation, a limited partnership, a service corporation, or a personal corporation.

The most an embodiment is described for requesting, performing, and reporting biological testing over a distributed computer network. The network includes remote user computers, a web server and order manager and a computer implementing a laboratory information management system (LIMS 106), which may be located at biological testing laboratory, or may be located elsewhere. Each of these is coupled together over a telecommunications network.

Remote user computers may be individual personal computers that are coupled directly to the telecommunications network. They may be located at the same facility, or they may be located at different facilities. They may be owned, operated, or controlled by the same entity, or by different entities. Computers may be joined together over a digital local area network (LAN) wherein the LAN provides access to telecommunications network through the interposition of an intermediate computer or computers.

Web server and order manager (hereinafter "web server") include one or more digital computers configured to serve web pages over telecommunications network to remote computers, to gather data from the remote user at remote user computer, to create an order for biological testing, and to communicate that order to LIMS 106. Web server is preferably located at a single facility. Alternatively, it may include one or more additional computers located at different facilities working in conjunction with one another.

LIMS 106 includes one or more digital computers configured with laboratory information management system (LIMS 106) software. It functions as a repository for data regarding samples to be tested and the test results for the samples, and may function to control automation of testing equipment, to track samples, to chart workflow, and to provide electronic data capture.

Telecommunications network may include public switched telephone networks (PSTN), wide area networks (WANs), and local area networks (LANS). It includes at least portions of a packet-switched public digital communication network such as the Internet.

Portions of telecommunication network may include communication devices that transmit analog signals. Digital data are superimposed on these analog signals such that all communications between remote user computer's and web server are of digital data.

Biological testing laboratory includes a plurality of automated digital test instruments that are configured to perform the biological testing requested by the remote user at remote user computers. The raw data from this testing is provided by the digital test instruments to LIMS 106, which in turn compiles the raw data into test results, and provides them to web server, which in turn provides them to the remote user at computers.

In an exemplary embodiment a remote user operating a remote user computer places a request over the telecommunications network to web server requesting biological testing of a plurality of biological samples. In response, web server is configured to transmit web pages to the remote user computer that determine whether the user is authorized to place an order by requesting a previously agreed upon password and account name. The remote user then responds via the remote user computer with the appropriate account name and password. In response to this, web server transmits a sequence of web pages that assist the remote user in identifying the particular biological samples she wishes to test. As the remote user receives the sequence of web pages and responds as directed, web server builds the user's order. When the remote user has completed her order and signals web server of that fact, web server transmits the completed order to LIMS 106 for further processing. This order creation process is described herein. The remote user then transmits the biological samples to be tested in one or more containers identified in the ordering process to laboratory. When the samples in their containers are received a laboratory, LIMS 106 compares the containers to identification data previously gathered by web server during the ordering process from the remote user.

Typical remote user computer includes at least one central processing unit in communication with a data storage device, a read-only memory (ROM), a random-access memory (RAM), a clock, a communications port, a printer, an input device, and a display. The processor is configured to be in communication with the data storage device, the read-only memory, the random-access memory, the clock, the communications port and the printer by means of a shared data bus or dedicated connections. The input device may be embodied, for example, as a keyboard, mouse, joystick or scanner or any combination thereof. The communications port connects the remote user computer to the telecommunications network, and thence to web server and LIMS 106. The communications port may include multiple communication channels for simultaneous communication with more than one terminal, display, and/or server. The communications port is configured to communicate with web server by receiving web pages and transmitting responses thereto.

Data storage device include one or more machine-readable media. Such media include, as is well-known in the art, an appropriate combination of magnetic, semiconductor and optical media, such as semiconductor memory circuits, optical disks, and magnetic disks. Storage device is preferably capable of supporting storing, searching and retrieving digital data in a variety of forms, including text, image, audio, and video formats. Data storage device also stores a plurality of digital instructions that configure processor to communicate over communications port with other computers are web servers in communication with telecommunications network. Among other things the plurality of digital instructions includes a web browser program for browsing the Internet that is configured to interoperate with web servers such as web server. When operating the web browser program, processor is configured to receive additional digital instructions from computers and web browsers coupled to remote user computer by communications port. These instructions, received from other computers and web browsers as a part of web communications, configure remote user computer to interoperate with these other computers and web browsers. The plurality of digital instructions may also be located in read-only memory and random-access memory.

Server typically includes memory and at least one processor in communication therewith and a communications port in communication with processor as well.

Memory typically includes one or more machine-readable media. Such media include, as is well-known in the art, an appropriate combination of magnetic, semiconductor and optical media, such as semiconductor memory circuits, optical disks, and magnetic disks. Memory is preferably capable of supporting storing, searching, and retrieving digital data in a variety of forms including text, image, audio, and video formats. In the present embodiment, memory includes an account database, an order database, a Test Name database, a probe database, and a user database. Memory also stores programs, which include digital instructions for controlling processor in accordance with the process described herein to serve web pages. These web pages are served to the remote user computer to confirm the user's identity and prompt the user to enter order information necessary for creating an order. Programs also include digital instructions for controlling processor to communicate with LIMS 106, to provide LIMS 106 with order information that web server both receives from the remote user in the manner described herein and calculates responsive to the data received from the remote user. Programs also include digital instructions for controlling processor to receive biological test results from LIMS 106 and to provide those test results to the remote user at remote user computer. Communications port may include multiple communication channels for simultaneous communication over network with a plurality of remote user computers. Communications port can communicate with the plurality of remote user computers by transmitting web pages to computers and receiving responses therefrom. Communications port can also communicate with LIMS 106 to provide data received from the remote users at remote user computers to LIMS 106.

An embodiment of LIMS 106 which includes at least one central processing unit in communication with a data storage device, a read-only memory (ROM), a random-access memory (RAM), a communications port, a printer, and input device, and a display. Processor is configured to be in communication with data storage device, read-only memory, random-access memory, communications port, printer, input device, and display device by means of a shared data bus, or dedicated connections. The input device may be embodied, for example, as one or more of a keyboard, barcode scanner, a mouse, a joystick, or a scanner. The communications port connects LIMS 106 to the telecommunications network, and thence to web server and remote user computers. The communications port may include multiple communication channels for simultaneous communication with more than one terminal, display, and/or server. The communications port can communicate with web server typically using a dedicated communications program, although LIMS 106 may include a Web browser.

Data storage device preferably includes one or more machine-readable media. This media includes, as is well-known in the art, an appropriate combination of magnetic, semiconductor and optical media, such as semiconductor memory circuits, optical disks, and magnetic disks. Storage device is preferably capable of supporting, storing, searching, and retrieving digital data in a variety of forms, including text, image, audio and video formats. Data storage device stores programs which include digital instructions for controlling processor in accordance with the process described herein to receive communications transmitted from web server including data identifying the accounts, the users, the orders, the Test Names, and the probes. This data is stored in account database, order database, Test Name database, user database, and probe database. LIMS 106 receives this data from web server which previously received this data from the remote user via remote user computer. The manner in which the user provides web server with the data is described in conjunction with the process. The databases in web server and LIMS 106 are substantial duplicates of each other. The ways in which databases update each other is well-known in the art.

Programs also control processor in accordance with the process described herein to communicate with the automated test equipment in biological testing laboratory. By doing this, processor provides the test equipment with instructions indicating the type and number of samples to be tested, and the tests to be performed. Generally speaking, LIMS 106 functions as a repository for data regarding samples to be tested and the test results for the samples, to control automation of testing equipment, to track samples, to chart workflow, and to provide electronic data capture. Any standard laboratory information management system software can be configured to be used to provide these functions. Alternatively, a standard relational database management system such as Oracle (Oracle Corp., Redwood Shores, Calif.) or SQL Server (Microsoft Corp., Redmond, Wash.) either alone or in combination with a standard LIMS 106 system can be used.

In accordance with the first embodiment of the invention, a computer-implemented method for ordering biological tests for biological samples is provided, the method includes the steps of: electronically populating one, or a plurality, of sample or patient specific information through an online portal system or electronic interface; electronically transmitting over the Internet the first plurality of patient information associated with the first biological sample to a LIMS 106 computer processor and associated systems configured to receive electronic order information for biological tests; and sending biological sample to a testing laboratory in a first package. The steps for a second biological sample for testing may include the step of electronically associating a second plurality of patient specific information with a second specific biological sample for testing. In the step of electronically transmitting may include the step of electronically transmitting over the Internet the second plurality of patient specific information with associated with the second specific biological sample to the computer.

The method may include electronically populating the plurality of sample (patient) specific information through an online portal/web-server system or electronic interface via manual entry of the plurality of patient specific information or by scanning, with a barcode reader the barcode, identification cards such as a student ID, work ID, drivers licenses or any other acceptable form of barcoded identification. See "Scan Patient Driver's License" button in the below image.

The step of sending the first biological sample may include the step of sending the second biological sample to the testing laboratory in the first package.

The method may include printing a physical label that is generated from a subset of the plurality of information that is associated with the first biological sample. The label is affixed to the sample tube containing the corresponding first biological sample. The first subset of the plurality of information that is associated with the first biological sample may be displayed as human readable, incorporated into barcoding on the physical label, or a mixture thereof. The printing of a physical label that is generated from a subset of the plurality of information that is associated with the second biological sample. The label is affixed to the sample tube containing the corresponding second biological sample. The subset of the plurality of information that is associated with the second biological samples may be displayed as human readable, incorporated into barcoding on the physical label or a mixture thereof.

The method may include labeling the first package with a preaddressed label having first indicia before the step of sending; wherein the step of electronically transmitting the first biological sample includes the step of electronically transmitting the first indicia to the computer over the Internet. The preaddressed label may include at least one identifier directing the shipping company handling the first package to automatically charge shipping costs to a first entity other than the entity performing the steps above. The method may further include the steps of placing the first biological sample in a tube rack; and placing the tube rack container into the first package before the step of sending the first sample.

The method may further include the steps of placing the first and second samples into a tube rack; and placing the tube rack container into the first package before the steps of sending the first and second sample. The method may further include the steps of electronically creating the first Test Name by electronically storing a name of the Test Name; and electronically storing a plurality of probes associated with the name of the first Test Name. The method may further include the steps of electronically transmitting the created first Test Name to the computer.

The method may further include the steps of electronically selecting a first probe from a plurality of probes; and electronically associating the first probe with the test name. The method may further include the steps of electronically selecting a second probe from the plurality of probes; and electronically associating the second probe with the test name. The test name may include a plurality of probes, and the method may further include the step of electronically deselecting at least one of the plurality of probes from the test name.

The computer may be configured to block completion of a biological sample order until all plurality of sample (patient) information for a biological sample has been completed. The method may include the step of receiving an automated e-mail notification that the sample tube has been received at the testing laboratory.

The method may include the step of receiving an automated e-mail notification that biological testing of a particular biological samples is complete. The method may include the steps of receiving an automated text containing a unique link. Upon clicking on the link, the user enters identifying information, such as the Date of Birth that corresponds to the Date of Birth in the plurality of specifically associated date for that particular sample. Upon entering the valid a date of birth, the biological sample result is displayed.

The test results may include a unique identifier of the sample tube container which was sent to the testing laboratory. The test results may include customer account information and contact information for the testing laboratory. The test results may include a date an order for testing biological samples was placed, a date the biological samples were received at the testing laboratory, and a date the biological samples was completed.

Figure 2:
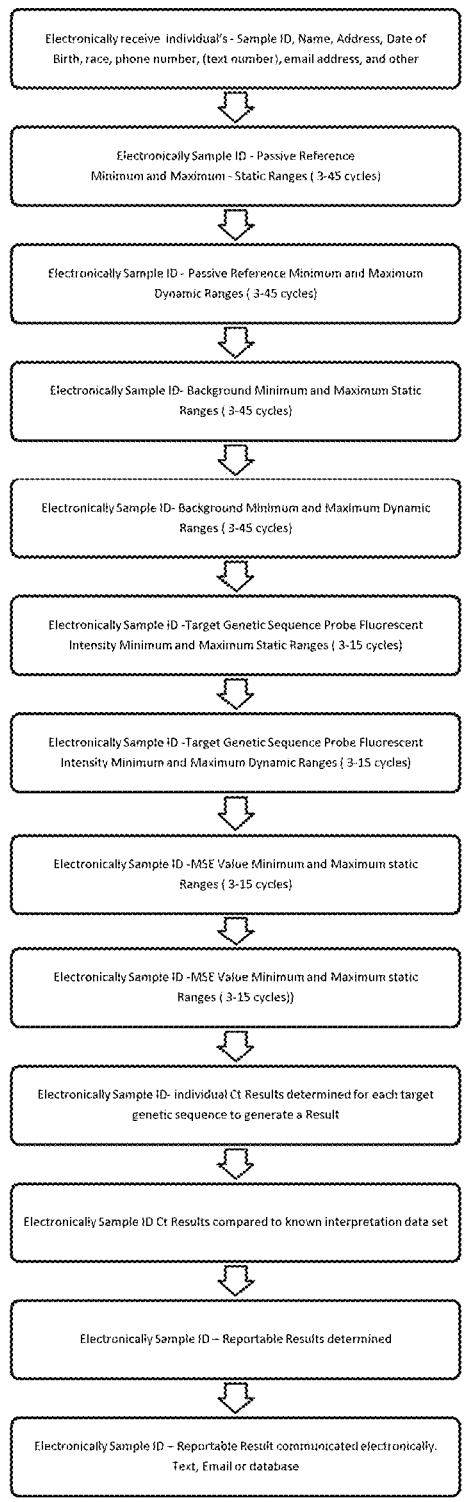
FIG. 2 shows the process of the present invention.

Now referring to FIGS. 1-2, a system for rapidly providing a reportable result to a user for the presence of a target nucleic acid sequence in a sample is shown. A remote client 101 includes a remote user computer including a CPU, and a memory, a RAM and a ROM wherein the computer is configured by a plurality of digital instructions to be operable to indicate a first biological sample for testing; to select a first plurality of associated information for the biological sample in a first sample order to be tested for the Test Name; and to transmit the information associated with biological sample to an second computer of an electronic system 120 including a computer configured to receive the plurality of patient specific information associated with the biological sample. The remote client 101 includes an electronic interface configured to transmit a plurality of patient specific information associated with a biological sample to the electronic system 120.

The Electronic System 120 is made of one or more computer, which contain one or more processors. These computers physically reside in one or more locations. Further, they are configured to utilize a network, such as the internet, to communicate information. The computers are configured to allow for connectivity and the execution of instruction to allow for specified configurations and types of automated electronic communication. The Electronic System 120 also includes a software systems such NETSOFTs (Snellville, Ga.) Intellipath system, or any Electronic Health record (EHR). An EHR is a digital version of a medical chart. EHRs are real-time records that make information available instantly and securely to authorized users. In one embodiment, after the LIMS system populates the Intellipath database with the appropriate information, including a test result, the Intellipath system automatically sends electronically information to the remote user via the electronic communication modality configured for that remote user. In the most preferred embodiment Intellipath can send the remote user a result directly via HL7 messaging to an established electronic interface with an outside organization (e.g., EHR to EHR). Alternatively, Intellipath can also be configured to electronically communicate testing results directly via fax or email. In another embodiment, Intellipath electronically sends a flat file to an Application Program Interface (API) of another computer that sends a text message to the remote user. Organizations, such as Twilio (Atlanta, Ga.), offer commercial text messaging services by allowing electronic connectivity to their computer systems.

The remote client 101 may be configured by the plurality of digital instructions to be operable to indicate a second biological sample for testing; to select a second plurality of specifically associated information with the second biological samples to be tested for the second Test Name; to transmit over the Internet the second Test Name associated with the second biological sample to the second computer of the electronic system 110.

The remote user computer of the remote client 101 may be configured by the plurality of digital instructions to be operable to create the first Test Name by storing a name of the first Test Name entered by an operator of the remote user computer; and to store a plurality of probes for selection by the operator of the remote user computer; to associate operator-selected probes of the plurality of probes with the name of the first Test Name; and to transmit the operator-selected probes to the second computer in association with the name of the first Test Name. The remote user computer may be configured by the plurality of digital instructions to be operable to permit an operator of the remote user computer to select a first probe from a plurality of probes, and to associate the first probe with the first Test Name. The first Test Name may include a plurality of probes, and further wherein the remote user computer is configured by the plurality of digital instructions to permit the operator to first select the plurality of probes by selecting the first Test Name, and then to deselect at least one of the plurality of probes from the first Test Name. The remote user computer may be configured by the plurality of digital instructions to be operable to permit an operator of the remote user computer to associate the biological samples with the first Test Name for testing. The remote user computer may be configured by the plurality of digital instructions to be operable to permit an operator of the remote user computer to associate the first biological sample with the first Test Name for testing; associate a second biological samples with the second Test Name for testing after the step of electronically associating the first biological sample.

The remote users at the remote user computers 101, web server 105, LIMS 106 106, and operators at laboratory are electronically connected via the electronic system 110 to order, perform, and report biological testing. The remote users operate remote user computers to request that laboratory perform biological testing upon a one or a plurality of biological samples. The remote user communicates this request to web server 105. Web server 105 receives this request and the details regarding the testing to be performed on the biological samples in a communications session made of a sequence of communications (preferably web pages and web page requests) transmitted back and forth between remote user computer 101 and web server 105 over telecommunications network. Once the user has provided web server 105 with the minimum required order data for creating an order, web server takes this order data from the remote user and transmits this order data to LIMS 106.

In another embodiment, the remote user's computers input device may be embodied, for example, as a keyboard, barcode scanner, mouse, joystick or scanner or any combination thereof. The communications port connects the remote user computer to the telecommunications network, and thence to web server and LIMS 106. The communications port may include multiple communication channels for simultaneous communication with more than one terminal, display, and/or server. The communications port is configured to communicate with by the user's relational databases such as Electronic Health Record (EHR) systems. There are many commercial patient relational database products in the market such as Cerner, and NextGen, which are embodiments of relational database communications with LIMS 106. The remote user's relational database is configured to transmitting information securely to the LIMS 106 over the network, often in a HL7 format.

At substantially the same time that the remote user places the order, the user also fills a sample container or containers with one or a plurality of samples that are to be tested, packages and seals the containers using materials previously provided by the biological testing laboratory, and transmits these samples to laboratory, typically via local courier or a commercial shipping company (such as DHL, UPS, or FedEx).

When laboratory receives the samples, the lab will have previously received an electronic record of the samples from web server or the remote user's relational database. An operator at laboratory opens the package containing the samples, electronically scans identifying data on the package into LIMS 106, and may electronically scan identifying data on the container in the package holding the samples. The data on the package and the container were already transmitted from the remote user to web server during the communications session between web server and remote user computer or database.

Components of a supply package for transmitting to the remote user, typically via local couriers that drive between locations, includes a box cooler enclosing, an empty sample tube rack, plastic biohazard bag which will enclose the tube rack once populated, a zip tie to close and secure the biohazard bag. In a separate supply package for transmitting to the remote user, typically via local couriers that drive between locations, includes a specimen bag, containing a sample collection container (e.g., sample tube containing transport media), and a sterile swab. Components of a supply package for transmitting to the remote user, occasionally are via US mail, FedEx, DHL, or UPS that includes a box (or package), including a specimen bag, containing a sample collection container (e.g., sample tube containing transport media), and a sterile swab.

Box coolers with its contents is sent from a supply depot (which is preferably co-located at laboratory) to the remote user before the user places an order for biological testing that uses container. As part of the ordering process, the remote user fills each well of container with samples, closes the sealing mechanism securely (e.g., screw top cap), places the sealed container inside the box in the tube rack and returns the box cooler with the samples back to laboratory for testing. In an embodiment, box cooler as returned by the user via local couriers, is not refrigerated or shipped in any specially cooled or heated medium. Instead, it is shipped using standard package shipping systems and the samples are permitted to fluctuate in temperature together with atmospheric temperature during shipment. Before sending the box cooler back to laboratory, however, the remote user transmits sample and order data to web server in response to the series of web pages presented by web server or the LIMS 106 receive this information directly from the remote user's database. In this manner, laboratory has a record of box cooler and all of the samples placed in the Tube Rack available when box cooler arrives at laboratory. Sample container is preferably a Sample Tube that has a screw top which is secured to prevent samples from leaking in transit. Moreover, strip racks, 96-well plates or the like may also be used. Other configurations such as linear or planar frame to which individual wells are small well assemblies may be attached also may be used. The container is marked with a unique indicium that uniquely identify the container. This indicium may be applied at the laboratory and supplied to the remote user, who will then incorporate this indicium into the electronic order for that sample. Alternatively, the container may be marked or labeled with the indicia when the electronic order is placed which in turn generates the indicia (e.g., barcodes or human readable) label 108 at the remote user's location, who then in turn applies this to the specific sample tube. The indicia are typically in the form of a barcode or other electronically scannable markings. They may also be in the form of electromagnetic device such as RFID tag that can be read by a radio transmitter/receiver.

The user places the sample in the container and then seals the container with a sealing mechanism like a screw top cap 110. The user then places the sample contain in the tube rack that is then placed inside a biohazard bag 112 and closed with a zip tie. The biohazard bag containing the tube rack and sample containers are placed in the cooler box and the lid is then closed. Subsequently, another unique identifier is applied to the outside of the cooler box that is electronically associated with samples container in the cooler box creating an electronic manifest of sample container for electronic chain-of-custody. In an embodiment, a courier is then contacted, and the cooler box is then retrieved from the remote user's location and the delivered to the testing laboratory.

Alternatively, if the remote user's location is deemed too far from the testing laboratory for local courier to transport, commercial transportations companies may be utilized (such as DHL, UPS, or FedEx). Regulatory compliant shipping materials and services are provided by the commercial transportation companies. Pre-addressed shipping labels are created with unique indicia on the shipping label that directs the shipping company to charge an entity associated with laboratory for the shipping costs, and not to charge the remote user or the remote user's institution identified in the remote user's account information. By automatically billing a laboratory related entity with the shipping costs, web server can be configured to automatically add shipping charges to the costs of every order it generates as a matter of policy, thereby obviating any human interaction to work out these details during each order. This streamlines the order creation process and further decreases errors. The physical pre-address shipping label is then affixed to the box (or package) that is used for shipping. The unique indicia on the shipping label (e.g., tracking number) is associated with the samples container when the electronic order is placed by the remote user.

Figure 3:
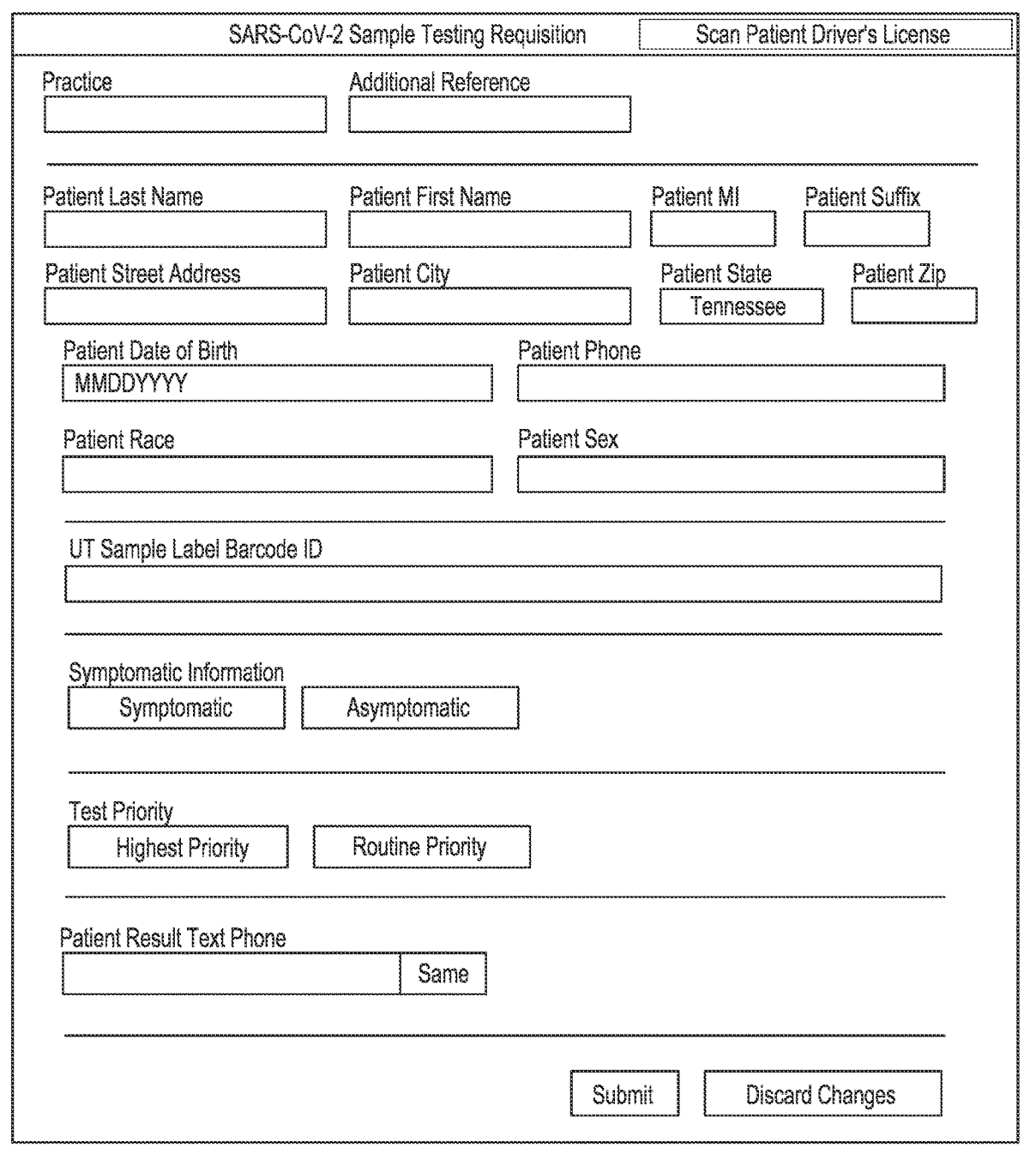

Now referring to FIG. 3, to place the order with web server and laboratory, the remote user operates computer, initiating the communications session with web server, entering data relating to the order, and then indicating that the order, has entered, is complete and correct. Once web server receives all the necessary order information, it transmits this information to LIMS 106. LIMS 106, in turn, gathers test results performed by testing laboratory and returns those results to web server, which then forwards them to the user at remote user computer.

Figure 4:
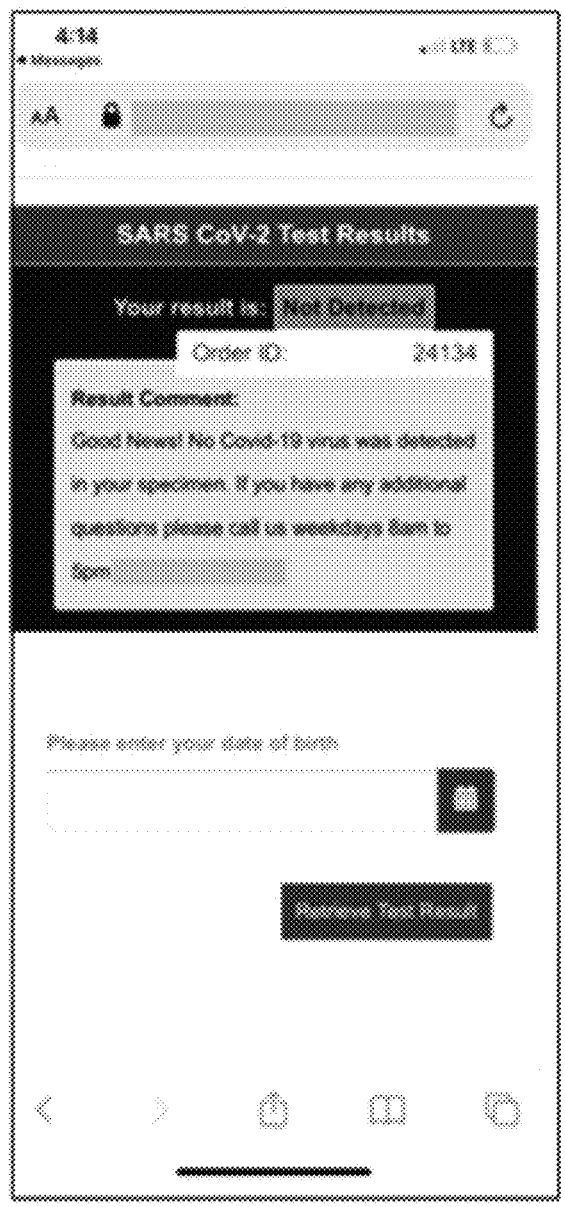
FIG. 4 shows an exemplary data input screen of the present invention.

Now referring to FIG. 4, a feature of the inventive subject matter is the process to allow patients to receive test results immediately. The remote user's web server is configured to indicate to the laboratory LIMS 106 system that text messaging of the results and/or emailing of the results is desired at approximately the same time the results data is transmitted to the remote user's database. LIMS 106 and associated mechanisms then act on that information received from the remote user's web server data transmission and a text message is sent to the indicated phone number, if indicated. That text message contains a unique link. The receiver of the text message is then required to enter their date of birth. The electronic mechanism then compares the dates of birth entered by the text recipient and the date of birth associated with the sample container. If there is a match of date or births the then test results will be displayed for the text recipient. If the birth date does not match another screen is displayed requesting the individual to contact the appropriate entity. Likewise, the remote user's web server order data transmission may indicate to LIMS 106 that results are to be emailed to a particular an email address. In such an event, at approximately the same time the results data is transmitted to the remote user's web server LIMS 106 and associated mechanisms then act on that information received from the remote user's web server data transmission and send an email containing the result to the indicated email address.

To place the order with the remote user's relational database to the laboratory, the remote user operates computer, initiating the communications session with its database (e.g., NextGen), entering data relating to the order, and then indicating that the order, has entered, is complete and correct. The remote user's database transmits this secure information to LIMS 106 in a manner such a HL7. LIMS 106, in turn, gathers test results performed by testing laboratory and returns those results to remote user's database. The remote user is not limited to entering all order information from a particular computer. Indeed, the remote user can save order information at one remote user computer (which is thereby communicated and stored at web server), then, can return at a later time to communicate with web server via a standard web browser on another remote user computer at the same patient, or a completely different location.

Image of the structure of web pages generated by web server in response to operator manipulation of input devices. The first of these web pages is the root web page to which the remote user first arrives. The second of these web pages is the account/password web page in which the user enters her account name and password to gain access to the remaining Web pages of the web site. The third of these web pages is the main web page from which the user may navigate to several other web pages.

The next web page is patient specific data and associated sample container web page. In this web page, the user can enter patients' specific demographics and other pieces of information, such as an option for text or email test results, and 'asymptomatic' or 'symptomatic' health status. The next web page is test results web page. This is the web page in which web server displays the test of results from completed order. Remote users can print test results as well as edit incorrect patient information, while maintaining a log of who and when any changes were made by the remote user. All the web pages are generated by web server in response to signals received from the remote user at remote user computer. The remote user selects any of a variety of selectable items that appear on his display, such as buttons, hypertext links, check boxes, radio buttons, and the like with input devices such as a barcode scanner mouse, keyboard, roller ball, or the like.

For ease of description, not every reference to the communication between remote user computer and web server states that the various web pages are generated (or regenerated in the same form or in a modified form) in response to signals generated by the remote user operating the remote user computer. This is the case, however. Whenever the user is described below as selecting or clicking or otherwise manipulating an item in a web page, it should be understood that a signal is transmitted from remote user computer to web server, which responsively generates or regenerates any web page that subsequently appears on display of remote user computer. Check boxes, radio buttons, and text boxes are filled or selected by the remote user operating keyboards or pointing devices of input devices remote user computer, and do not necessarily send a signal to web server. The same understanding should also be made for the relational database ordering embodiment.

The first step is connecting to the web server. In the step, the remote user seats herself at remote user computer, and executes a Web browser program such as for example INTERNET EXPLORER (Microsoft Corporation). Once the remote user executes a Web browser program, she enters the initial URL of the web pages served by web server. In an embodiment, this is a root domain of a web site.

Once the user has entered the initial URL and transmitted it to web server, web server responds by transmitting a web page corresponding to the initial URL back to the remote user. Web browser is configured to transmit each successive web page back to computer to appear in the same window unless otherwise noted herein. Thus, the initial web page transmitted by Web browser appears in the same Web browser window in which the user previously typed the initial URL.

The root web page appears in window of a commercial Web browser. The web page includes a button which the user can click using the input device of remote user computer in order to gain access to the succeeding web pages served by Web browser. When the user selects button, web browser responds by transmitting account/password entry web page. The account/password web page includes a text box for the user to enter an account name, here labeled as "Email:", a text box for the user to enter a corresponding password, a button for submitting the data in web page to web server, a checkbox for selecting whether or not to store a browser "cookie" on the remote use computer, a button for retrieving a lost password, a button for registering a new account (in the event the remote user does not currently have an account), and a text region for listing several frequently asked questions. In response to this web page, the user enters the account identifier or name into text box, a corresponding password into text box, and clicks submit button. Upon receiving this data, web server compares the supplied account identifier and password with the electronic records in its account database and the user database to determine whether there is a valid account associated with the remote user having that name having that password. If not, web server responsively transmits an error message to the user indicating that the password and account name or incorrect. If the password and account name are valid, however, web server responsively transmits the next web page. A main web page provides the user with several additional selectable choices not originally provided in the initial web page. Among these include a selection that permits the remote user to view past orders, pending orders, and completed orders for biological testing, a selection that permits the remote user to place a new order for biological testing.

In an embodiment, the biological tests that are performed on the samples are genotyping tests, in which the tests determined the presence or absence of a specific genetic sequence or sequences that indicate the biological sample contains pathogenic viral sequences. Once the remote user logs on to web server by entering the appropriate account name and password, she is given access to all of these predefined Test Names. As will be described below, web server is configured to automatically associates the primers, probes, and primer/probe sets (hereinafter collectively referred to as "probes") associated with those Test Names.

Probes are required to determine the presence of genetic sequences comprising the Test Name. In order to screen for particular genetic sequences (such as the ones defining the Test Name), those sequences must first be determined. Only when the designated genetic sequence or sequences are identified can a test to be devised to search for the existence of the sequences in the biological samples provided by the remote user to laboratory. There are a variety of ways that these designated genetic sequences can be acquired by the remote user or by laboratory. For example, if the sequences of bases that make up designated genetic sequences are known by the remote user, these sequences can be directly communicated to laboratory, such as to web server in a web page (not shown), by e-mail, or via telephone. The remote user can indirectly communicate the designated genetic sequences to laboratory by communicating the name of a publication, Journal article, gene name, sequence name, or the name of a line or strain (if the designated genetic sequence is found in animals of that line or strain), or the name of a mutation having the designated genetic sequences. Alternatively, the remote user can communicate to laboratory the sequence of a primer set or probe that corresponds to a target genetic sequence of the designated genetic sequence that defines the Test Name.

In any event, whatever the genetic sequence or sequences that define the Test Name for which the samples are tested, a probe either exists or can be created to sense the presence of those genetic sequences (or unique portions of those genetic sequences) in the samples. The process of identifying the genetic sequences that define the Test Name, determining the probes that can sense the genetic sequences, and validating the probe by testing it on biological test samples is beyond the scope of this invention, and therefore is not described in detail herein.

In some cases, the user may not wish to submit the order to web server even after all the order information has been added. The remote user may not be authorized to place orders, for example, and thus may wait for a third-party to examine the order, confirm that it is correct, and then press button to place the order and button to confirm the order.

To permit the user or other personnel to return to the order and complete at a different time, web server maintains an order database that identifies the order, the samples to be tested the individual tests to be performed on the samples, the containers, and indicia of the containers in which the samples will be sent.

The order database includes this data for all orders, including orders that are incomplete (e.g., orders that have not yet been placed with web server), those that are being processed (e.g., orders that have been placed with web server), and those that have been fulfilled by laboratory (e.g., orders which laboratory has finished testing and has reported out test results to web server).

To access this order database, view any of the orders listed therein, and submit any incomplete orders to web server, the user returns to main web page and clicks on button. When the user does this, web server responsively generates web page.

The remote user can view all the orders created by all of the authorized users. The remote user can change the authorized users' orders or submit the authorized users' orders. The primary role of the remote user is to administer the account, and correct errors and change data entered by individuals logged in as different authorized users. For this reason, the remote user must have access to view and modifying all of the sub-users and their activity, which it is given by web server.

To add an authorized user (i.e., sub-user) the remote user clicks on button which is displayed in the bottom of user list. When the remote user clicks on button, the remote user computer is configured to transmit a signal to web server, indicating that the remote user would like to create an authorized user. In response, web server generates a pop-up window displaying the create user web page.

Create user web page includes a text box for entering a new authorized users first name, a text box for entering a new authorized user's last name, and a text box for entering the e-mail address of the new authorized user. Web page also includes a submission button, which, when pressed signals remote user computer to transmit the data in web page web server. Web server responsively creates an e-mail message that it sends to the e-mail address indicated in text box.

This e-mail message offers the new authorized user the opportunity to create an authorized user identity on web server, which will allow the authorized user to create orders in the remote user's account and will also permit the authorized user to submit those orders to web server in the same manner described above for the remote user. It indicates the domain name of web server, indicates the account name the proposed new authorized user will use (preferably her e-mail address), and indicates the password associated with that account name. Web server is configured to generate passwords whenever a remote user creates a new authorized user. This password is not communicated to the remote user, and therefore the remote user cannot access web server by assuming the identity of another authorized user.

When web server receives the name and e-mail address of the proposed new authorized user, it also creates an entry in the user database in web server. This database associates the name and e-mail address of the new authorized user proposed by the remote user with the remote user's account. It also indicates that the proposed remote user is not yet registered—i.e., has not yet logged on to web server a first time to gain access. Once the remote user has requested the creation of a new authorized user, whenever web server transmits account management web page, it will update it, showing the new remote user in the authorized user list. A typical authorized user is shown in the authorized user list. Logging on to the system is essential to becoming a full participant in the remote user's account. Once a proposed new authorized user logs on to web server using the account name and password provided by web server in the e-mail message, web server responds by changing the status of that authorized user to "Registered". Thenceforth, when the remote user reconnects to web server, logs on, and displays web page again, web server will display that authorized user with their new status of "Registered". Eventually, laboratory will perform the tests indicated in the order that the remote user placed. When the tests on each of the samples are complete, the results are gathered by LIMS 106 and compiled. LIMS 106 then sends the test results to web server, which enters them in its order database.

When the remote user initially created the order, the remote user transmitted the order information via relational database or web server, which saved the order information in its order database. This data includes the indicia of container in which the sample was inserted. Web server is configured to automatically retrieve this information from its order database and to incorporate this information into the test results.

For example, although databases have been identified for web server and LIMS 106, the data in these databases can be combined into fewer databases, including a single database, or can be further subdivided into a greater number of sub-databases. Furthermore, individual databases can be combined, and elements of each database can be moved from one database to another. Thus, a portion of any of the described databases can be incorporated into another database.

As another example, LIMS 106 is shown located at laboratory. LIMS 106 need not be located at laboratory, however, but can be located elsewhere and in communication with laboratory and with web server over a LAN, WAN, or the Internet.

As yet another example, the computers and servers described herein are each shown as software and data existing on a single computer. In an alternative embodiment, each may be comprised of multiple computers, with each computer performing a portion of the functions identified for the computers and servers.

Even further, while the description above relates to a particularly an application of biological testing, that of genotyping using Test Names and probes, the identical process can be used with other forms of biological testing, and even genotyping using profiles and primer sets. In such case, instead of having a Test Name database and associated probes, web server would have a profile database and manipulate Profiles (in place of the Test Names, above), and would have a primer set database and manipulate primer sets. Alternatively, animal Lines and Strains would have a primer and probe set database and manipulate primer and probe sets. Genotyping with Next Generation Sequencing (NGS), primer and index set would be in the database and manipulation of the primers and index set may be necessary for some applications.

In an embodiment illustrated above, the user at remote user computer interacts with a web server. Web communication over the Internet is a mode of placing an order. Dedicated programs and databases, however, can communicate the same information between remote user computer and another computer such as web server, that need not be configured to communicate with remote user computer as a web server, however. Instead, dedicated programs and databases operating on computer can communicate the same information back and forth between remote user computer and computer over the Internet, as seen in the relational database embodiment.

If LIMS 106 is not located at test laboratory, additional computers at test laboratory can be configured to communicate over network with LIMS 106, to communicate information to LIMS 106 such as the identifiers or indicia on cooler boxes and sample containers shipped to testing lab from the remote user and containing her order. In an embodiment, all the web pages are described as being generated by "web server". In an alternative embodiment, web server may be a plurality of individual web servers each providing a different web page. In another alternative embodiment, these individual web servers may be disposed at different locations, and communication between the remote user computer and web server may include transmissions from remote user computer to two or more different physical computers located at two or more different locations, each one of which can perform any one or more of the functions described above as being performed by web server.

In the preferred embodiment, the biological tests that are performed on the samples are genotyping tests, in which the tests determined the presence or absence of a specific genetic sequence or sequences that indicate the biological sample contains pathogenic viral sequences. Once the remote user logs on to web server by entering the appropriate account name and password, she is given access to all of these predefined Test Names. As will be described below, web server is configured to automatically associates the primers, probes, and primer/probe sets (hereinafter collectively referred to as "probes") associated with those Test Names.

Probes are required to determine the presence of genetic sequences comprising the Test Name. In order to screen for particular genetic sequences (such as the ones defining the Test Name), those sequences must first be determined. Only when the designated genetic sequence or sequences are identified can a test to be devised to search for the existence of the sequences in the biological samples provided by the remote user to laboratory. There are a variety of ways that these designated genetic sequences can be acquired by the remote user or by laboratory. For example, if the sequences of bases that make up designated genetic sequences are known by the remote user, these sequences can be directly communicated to laboratory, such as to web server in a web page (not shown), by e-mail, or via telephone. The remote user can indirectly communicate the designated genetic sequences to laboratory by communicating the name of a publication, Journal article, gene name, sequence name, or the name of a line or strain (if the designated genetic sequence is found in animals of that line or strain), or the name of a mutation having the designated genetic sequences. Alternatively, the remote user can communicate to laboratory the sequence of a primer set or probe that corresponds to a target genetic sequence of the designated genetic sequence that defines the Test Name.

In any event, whatever the genetic sequence or sequences that define the Test Name for which the samples are tested, a probe either exists or can be created to sense the presence of those genetic sequences (or unique portions of those genetic sequences) in the samples. The process of identifying the genetic sequences that define the Test Name, determining the probes that can sense the genetic sequences, and validating the probe by testing it on biological test samples is beyond the scope of this invention, and therefore is not described in detail herein. In some cases, the user may not wish to submit the order to web server even after all the order information has been added. The remote user may not be authorized to place orders, for example, and thus may wait for a third-party to examine the order, confirm that it is correct, and then press button to place the order and button to confirm the order. To permit the user or other personnel to return to the order and complete at a different time, web server maintains an order database that identifies the order, the samples to be tested the individual tests to be performed on the samples, the containers and indicia of the containers in which the samples will be sent. The order database includes this data for all orders, including orders that are incomplete (e.g., orders that have not yet been placed with web server), those that are being processed (e.g., orders that have been placed with web server), and those that have been fulfilled by laboratory (e.g., orders which laboratory has finished testing and has reported out test results to web server). To access this order database, view any of the orders listed therein, and submit any incomplete orders to web server, the user returns to main web page and clicks on button. When the user does this, web server responsively generates web page.

The remote user can view all the orders created by all of the authorized users. The remote user can change the authorized users' orders or submit the authorized users' orders. The primary role of the remote user is to administer the account, and correct errors and change data entered by individuals logged in as different authorized users. For this reason, the remote user must have access to view and modifying all of the sub-users and their activity, which it is given by web server.

To add an authorized user (i.e., sub-user) the remote user clicks on button which is displayed in the bottom of user list. When the remote user clicks on button, the remote user computer is configured to transmit a signal to web server, indicating that the remote user would like to create an authorized user. In response, web server generates a pop-up window displaying the create user web page. Create user web page includes a text box for entering a new authorized users first name, a text box for entering a new authorized user's last name, and a text box for entering the e-mail address of the new authorized user. Web page also includes a submission button, which, when pressed signals remote user computer to transmit the data in web page web server. Web server responsively creates an e-mail message that it sends to the e-mail address indicated in text box.

This e-mail message offers the new authorized user the opportunity to create an authorized user identity on web server, which will allow the authorized user to create orders in the remote user's account and will also permit the authorized user to submit those orders to web server in the same manner described above for the remote user. It indicates the domain name of web server, indicates the account name the proposed new authorized user will use (preferably her e-mail address), and indicates the password associated with that account name. Web server is configured to generate passwords whenever a remote user creates a new authorized user. This password is not communicated to the remote user, and therefore the remote user cannot access web server by assuming the identity of another authorized user.

When web server receives the name and e-mail address of the proposed new authorized user, it also creates an entry in the user database in web server. This database associates the name and e-mail address of the new authorized user proposed by the remote user with the remote user's account. It also indicates that the proposed remote user is not yet registered—i.e., has not yet logged on to web server a first time to gain access.

Once the remote user has requested the creation of a new authorized user, whenever web server transmits account management web page, it will update it, showing the new remote user in the authorized user list. A typical authorized user is shown in the authorized user list.

Logging on to the system is essential to becoming a full participant in the remote user's account. Once a proposed new authorized user logs on to web server using the account name and password provided by web server in the e-mail message, web server responds by changing the status of that authorized user to "Registered". Thenceforth, when the remote user reconnects to web server, logs on, and displays web page again, web server will display that authorized user with their new status of "Registered".

Eventually, LIMS 106 and potentially other associated electronic systems will compile and execute all the tests indicated in the electronic order that the remote user placed. In one embodiment, the electronic processors in the LIMS 106 electronic informatics system are configured to create unique electronic files that are sent over a network to laboratory instrumentation. The laboratory instrumentation processors and software program are configured in a manner that allows for the importation and interpretation of the LIMS 106 electronic information to confer electronic chain-of custody.

In an exemplary embodiment, the electronic chain of custody is conferred by the remote user gaining access to the web server and electronically populating sample (e.g., patient) specific information through the online portal/web-server system or electronic interface. To ensure rapid, accurate sample specific information a barcode reader is utilized to capture the information encoded in the barcode of suitable Identification Cards, such as a Student Identification, Work or Employer barcoded ID, Military ID, Drivers Licenses or any other acceptable form of barcoded identification. Once the samples information is acquired a physical barcoded label is printed that contains minimally a subset of the samples specific information that was electronically captured. Further, additional information, such as unique accession number, are auto generated and associated only with this sample and all the electronic information is transmitted to the laboratory through the web portal, or electronic interface. The barcode physically printed on the label contains information encoded into the barcode, as well as human readable information. The encoded barcode information and human readable information printed on the label includes minimally a unique subset of sample information and/or auto-generated information. Once printed the label is then affixed to the corresponding sample container at the remote user's location. A physical label is attached to the sample container. The physical label includes sample specific data and a machine-readable code such as a bar code. The sample is tracked by the laboratory instrumentation by scanning the machine-readable code.

The samples containers are then sent to the laboratory, who has previously received an electronic manifest from the web portal, or interface, of the anticipated incoming uniquely identified sample containers. During the receiving process of the samples at the laboratory, the unique barcode is scanned for each sample container. This process is repeated for each sample until all the samples containers are electronically timestamped and verified as being present in the laboratory in the electronic LIMS 106 system. If a sample container has an electronic order record transmitted from the remote user to the laboratory, but no physical specimen arrives, then the remote user will be notified that the laboratory did not receive the physical sample despite the electronic order.

The sample container's barcode is scanned while the sample container is placed in a discrete location on the laboratory's information. The electronic LIMS 106 system contains each sample containers electronic information and records, via barcode scanning, the specific location and associated electronic data generated by the different pieces of the laboratory instrumentation.

The combination of the rapid and accurate acquisition of sample specific information, the unique sample information encoded in the sample containers barcode, the corresponding data generated from the laboratory information, and the one or more electronic processors that amalgamates all the electronic information and associated data and transforms the information and data into a rapidly reportable result in an automated manner, and a mechanism to deliver electronically (e.g., text message, email etc.) the automated real-time reportable result to the remote user is significant and advantageous over traditional laboratory practices. The laboratory LIMS 106 processors then receive electronic data files from the laboratory instrumentation during or upon complete of the instrument run. The laboratory LIMS 106 processors are then utilized to interpret the instrument data files to automatically, or semi-automatically, interpret the sample result with maintaining full chain of custody. Further, the LIMS 106 processors are configured to automatically send electronic text messages and/or emails to patients and/or client organizations.

Example: In one embodiment, the SARS-CoV-2 RT-PCR high throughput assay is used for the diagnostic qualitative detection of ribonucleic acid from the SARS-CoV-2 virus in nasal swabs from individuals suspected of COVID-19 by their healthcare provider. The SARS-CoV-2 RNA is generally detectable in upper respiratory samples during the acute phase of infection. Positive results are indicative of the presence of SARS-CoV-2 RNA. The oligonucleotide primers and probes for detection of SARS-CoV-2 were selected from regions of the virus nucleocapsid (N) gene. The panel is designed for specific detection of the 2019-nCoV (two primer/probe sets). An additional primer/probe set to detect human RNase P gene (RP) in control samples and clinical samples is included in the panel. RNA isolated and purified from nasal swabs is reverse transcribed with TaqPath 1-Step RT-qPCR Master Mix (ThermoFisher Catalog #A15299 or A15300) to cDNA and subsequently amplified with primers and probes (Integrated DNA Technologies, Coralville, Iowa) in ABI 7900 HT Real Time PCR System (Applied Biosystems, Foster City, Calif.) with SDS Software (Version #2.4) which is an example of an automated laboratory instrumentation 114.

In the process, the probe anneals to a specific target sequence located between the forward and reverse primers. Primers and probes: 2019_nCoV_NI| 2019-nCoV_NI Combined Primer/Probe Mix| IDT Catalog #10006600 2019_nCoV_N2 |2019-nCoV_N 2 Combined Primer/Probe Mix | IDT Catalog #10006601 RPI Human RNase P Forward Primer/Probe Mix | IDT Catalog #10006603.

During the extension phase of the PCR cycle, the 5' nuclease activity of Taq polymerase degrades the probe, causing the reporter dye to separate from the quencher dye, generating a fluorescent signal. With each cycle, additional reporter dye molecules are cleaved from their respective probes, increasing the fluorescence intensity. Fluorescence intensity is monitored at each PCR cycle by ABI 7900 HT Real Time PCR System with SDS Software V2.4. Fluorescence reporter dyes include FAM, ROX, JOE, TET, VIC, TAMRA, Yakama Yellow, Cyanine dyes, Alexa dyes or any analogous dye that is detectable in the spectral range of the instrument is suitable. Any fluorescent reporter dye can be used as a Passive Reference Dye or for labeling of the PCR probe.

The laboratory LIMS 106 processors are configured to send the electronic messages to the instrumentation processor and the processors of the instrumentation configuration receive and act upon the electronic messages. The electronic messages may include instrument setting. Specifically, the instrument setting may include: Creation of the Covid19 PCR.sdt blank template with detectors for each primer/probe combination, analysis settings and thermal cycler conditions are saved.

a. Analysis Settings:
   i. Threshold at 0.05. Threshold is set at the geometric phase of the growth curve.
   ii. Background from 3 to 15 cycles
b. Thermoprofile Settings:
   i. In Stage 1, set to 2 min at 25° Celsius, 1 repetition.
   ii. In Stage 2, set to 15 min at 50° Celsius, 1 repetition.
   iii. In Stage 3, set to 2 min at 95° Celsius, 1 repetition.
   iv. In Stage 4, Step 1 set to 3 sec at 95° Celsius
   v. In Stage 4, Step 2 set to 30 sec at 55° Celsius
   vi. In Stage 4, repetitions are 45

The LIMS 106 electronic messaging executes the CovID19 LabVantage PCR.sdt template on the SDS 2.4 software. The processors of the instrumentation automatically act upon the electronic messaging from the LIMS 106 processors by receiving the electronic information (e.g., CovID19-PCR-Pla-200xxx-0000x.txt experiment plate map that was created by LIMS 106 system). The LIMS 106 processors create electronics information that has sample unique identifier, detector names and detector position for each sample and primer probe set. The instrumentation saves the file (e.g., CovID19-PCR-Pla-200xxx-0000x.sds.). The associated testing instrumentation is loaded with the samples and the instrumentation file is executed and data subsequently analyzed.

Figure 5:
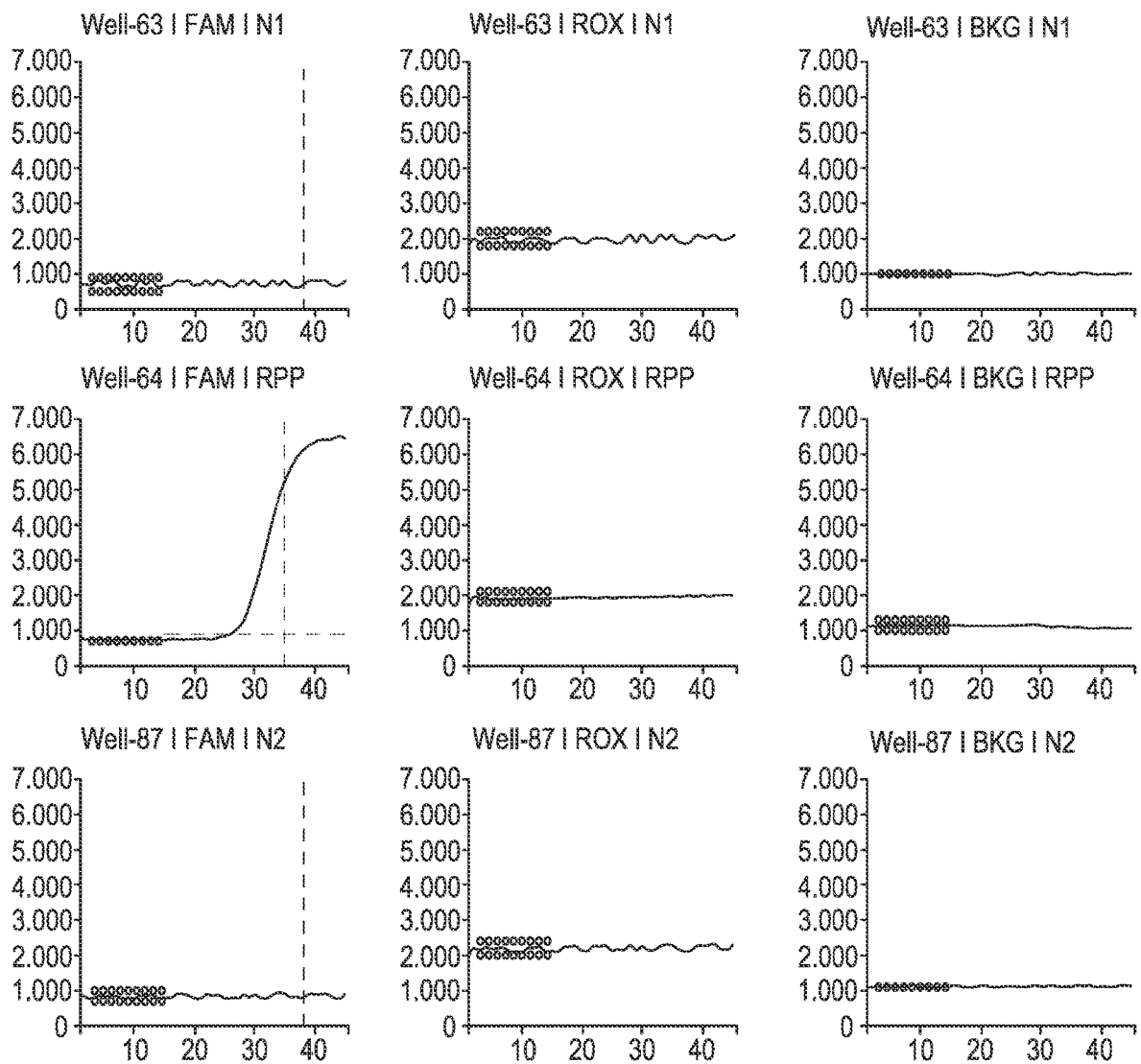
FIG. 5 shows the validation process of the present invention.
Figure 6:
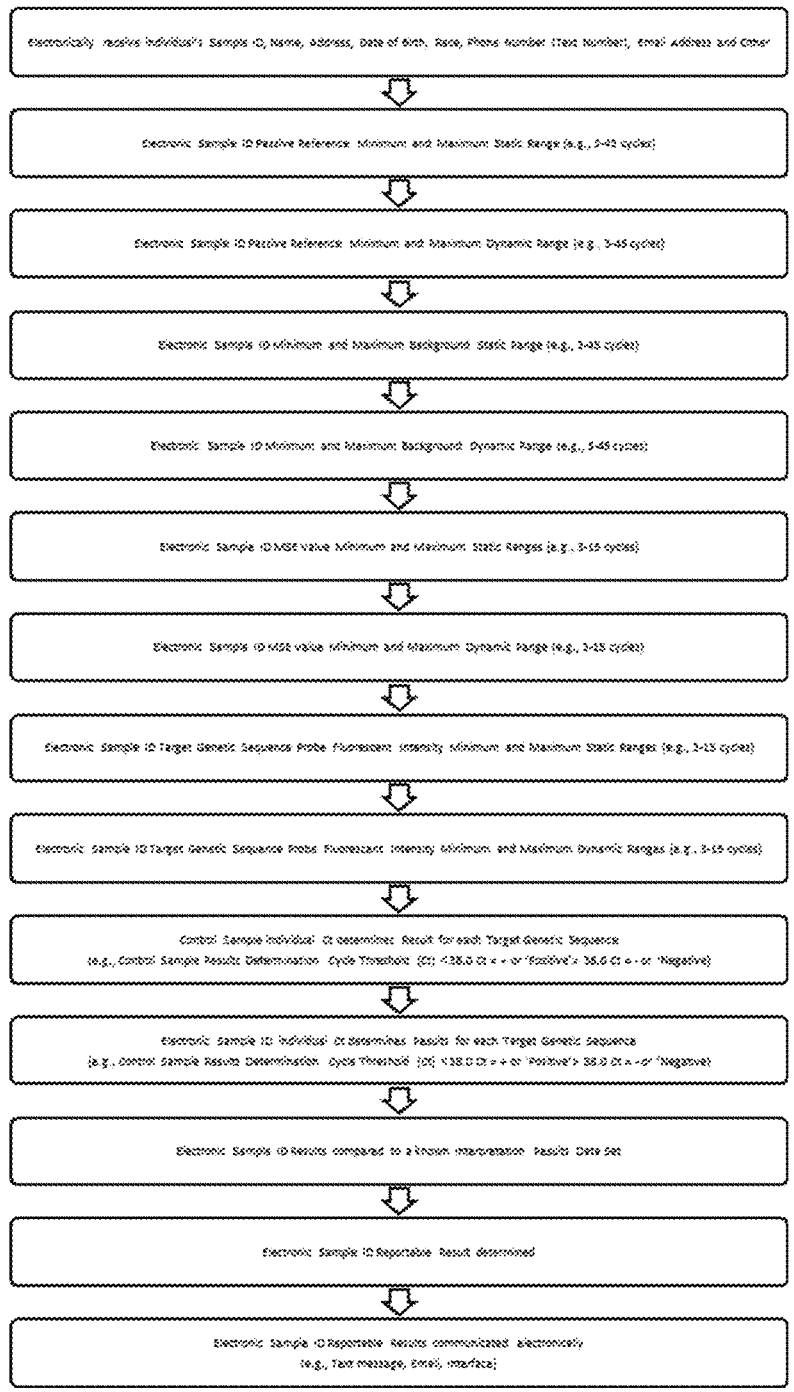
FIG. 6 shows the fluorescent intensity data at each PCR cycle of the process for FAM (e.g., for target genetic sequences), ROX (e.g., Passive Reference dye) and Background.

Now referring to FIGS. 5-6, the LIMS 106 processors and associated electronic system executes a stepwise algorithm that allows for determination of sample results by each well of a sample to pass stringent criteria based on:

1. Each sample's (including control samples) fluorescent intensity being within the fluorescent intensity static ranges,
2. Each sample's (including control samples) fluorescent intensity being within the fluorescent intensity dynamic ranges,
3. Each sample's (including control samples) cycle threshold values being within the established cycle threshold values ranges for positive and negative results.
4. Each sample's (including control samples) positive and negative results being compared to know positive and negative reportable result combinations.

TABLE 1

Reportable Results Combinations:

| 2019 Coy-N1 | 2019 Coy-N1 | RP | Reportable Result |
|---|---|---|---|
| + | + | + | Detected |
| + | + | − | Detected |
| + | − | + | Inconclusive |
| − | + | + | Inconclusive |
| − | − | − | Invalid |
| − | − | + | Not Detected |

The instrumentation processors record the fluorescence intensity at each PCR cycle in the SDS data. The instruments electronic SDS files are analyzed, for defined quality check points for the instrument setting the LIMS 106 processors. The LIMS 106 processors received the electronic information and data from the associated testing instrumentation and acts upon that electronic communication in an automated manner for these quality checks. The post-instrument-run quality check points include processors electronically evaluating the electronic data files to confirm that the proper instrument settings were utilized to generate the electronic data. The LIMS 106 processors execute commands that enables the automated analysis of the post-instrument-run. The data automatically evaluated during the post-instrument-run includes proper: Filename structure (e.g., CovID19-PCR-Pla-200xxx-0000x.sds.); Assay Type: (e.g., Absolute Quantification); Baseline Type: (e.g., "Manual"); Baseline Start: (e.g., "3") Baseline Stop: (e.g., "15") Threshold Type: (e.g., "Manual") Threshold: (e.g., "0.05") Passive Reference Dye: (e.g., ROX). Other post-instrument-run quality checks may include the automatic confirmation that the proper instrument thermoprofile was run. The proper thermoprofile may include the proper Time Stamps, the proper Temperature, the proper number of Cycles, Steps and Repeats per sample.

The computer processors electronically evaluating the fluorescent intensity data for each detector being utilized. This includes fluorescence intensity data associated with probe for the target genetic sequences of interest in a sample, Passive Reference Dyes, Background and MSE values. The fluorescence intensity values are used by the LIMS 106 processors and subsequent configurations to evaluate subsets of data or information, perform dynamic calculation of minimum and maximum allowable thresholds. The calculation may be any statistical calculation. For example, a calculation such as 3.5 Standard Deviation above and below the average fluorescence intensity over the course of the PCR cycles is used to determine the minimum and maximum allowable dynamic thresholds. The value set between the dynamically generated minimum and maximum thresholds is referred to as the 'dynamic value range', as well as observe other static minimum and maximum allowable thresholds. The value set between the static minimum and maximum allowable thresholds is referred to as the 'statics value range'. Subsequently, samples that are found to be within the static and dynamic limits created by the LIMS 106 processors will be moved to the sample evaluation analysis. Alternatively, if a sample is found to have associated fluorescence intensity values that fall outside the dynamic ranges generated by the LIMS 106 processors or the statics ranges, then those samples will be identified for manual or semi-automated review.

The fluorescence intensity data associated with samples include the Passive Reference Dyes, Genetic Targets in a sample, Background and MSE values. LIMS 106 processors and systems identify samples whose fluorescence intensity data falls outside and inside the dynamic and statics ranges. Note that this is one example configuration of fluorescent detectors and combination of detectors (e.g., multiplex PCR) which can easily be changed, substituted for other dye(s) and added/removed for the Passive Reference Dyes and Genetic Targets in a sample.

LIMS 106 processor and system determine the fluorescent static value ranges and dynamic value ranges utilizing the electronic instrument files fluorescent intensity data. Note that sample analysis is not limited to within LIMS 106 and can be performed by computer processors, systems and programs that exist outside a LIMS 106 environment. Each biological sample has a plurality of wells, such as for example three wells, which are each associated with a different target genetic sequence. The three target genetic sequences, are indicated as 'N1', 'RP', and 'N2'. Each of the different target genetic sequence fluorescent intensity values are represented by three graphs (vertically). The fluorescent intensity values are expressed as Relative Fluorescent Units (RFU) on the Y-axis of each chart. The fluorescent intensity values are a unit of measurement used in analysis which employs fluorescence detection. A computer program measures the results, determining the quantity at each data point, from the level of fluorescence intensity. Samples which contain higher quantities of amplified DNA will have higher corresponding fluorescent intensity values value. The X-axis of each chart indicated the number of PCR cycles. The small, round dotted line that extends the entire length of the X-axis for FAM indicates the cycle threshold (Ct). In a real time, PCR assay a positive reaction is detected by accumulation of a fluorescent signal. The 'sample cycle threshold' (Ct) is defined as the number of PCR cycles required for the fluorescent signal to cross the threshold (i.e., exceeds background level). The sample cycle threshold is expressed as a numeric value, referred to as the sample cycle threshold value. Cycle threshold values are inversely proportional to the amount of target nucleic acid in the sample (i.e., the lower the Ct level the greater the amount of target nucleic acid in the sample). In FIG. 5, the probes for 'N1', 'RP', and 'N2' are labeled with the fluorescent dye FAM, each is in a different well and corresponds to different target genetic sequence.

In this exemplary example, each biological sample has three wells, each of which also contains one or more Passive Reference Dyes (e.g., ROX), that are fluorescent, and combined with different PCR reactants to ensure all the PCR reaction components were in each well at the time of the PCR reaction. The Passive Reference Dye fluorescent intensity is associated with each well for the different target genetic sequences. Each of the Passive Reference Dyes associated with the different target genetic sequence are represented by the three middle graphs (vertically) in FIG. 5.

The LIMS 106 Processor and associated electronic system creates and applies the dynamic value range for each well based on the dynamic minimum and maximum thresholds calculation, as indicated by partial lines of large square shaped dots on each graph for the three samples wells in FIG. 5.

Passive Reference Dye—(e.g., ROX) identify any sample well that from Time 2464 and 55.0 (Temp) from (Repeat 3-45), as seen in the instrument data files, varies as follows: Note the instrument file referees to the PCR 'Cycle' as 'Repeat'. The terms are used interchangeably. Any Repeat ROX fluorescence intensity value less than a determined static value (e.g., 1,500) and/or any Repeat ROX fluorescence intensity value greater than a determines static value (e.g., 10,000) at any cycle is flagged for manual or semi-automated review and data for all three wells for this individual sample and is removed from further steps in the process.

Passive Reference dye's—(e.g., ROX) fluorescence intensity values that statistically vary, at any cycle, by more or less than the established dynamic value range (e.g., 3.5 Standard Deviations) is flagged for manual or semi-automated review and data for all three well for this individual sample is removed from further steps in the process. Specifically, this is done in an electronic manner for the ROX by comparing, by the one or more processors, a plurality of sample fluorescent intensity values against the dynamic value range and the static value range. If any wells fluorescence intensity values, during the defined PCR cycles, falls outside the dynamic value range and/or the static value range, the sample is flagged for manual or semi-automated review.

Target Genetic Sequence Probe in a Sample—(e.g., FAM monoplex; if multiplexed FAM/Joe, etc.) One or more processors identify any sample well that (from Time 2464 and/or 55.0 (Temp) from Repeat 3-15) has any Repeat FAM fluorescence intensity value, less than a determined static value range (e.g., 1,500) and/or has any Repeat FAM fluorescence intensity value, greater than a determined static value range (e.g., 10,000). If so, the sample is flagged for manual or semi-automated review and data for all three well for this individual sample is removed from further steps in the process. FAM fluorescence intensity values that statistically vary by greater than or less than an established dynamic range of fluorescence intensity values (e.g., 3.5 Standard Deviations) for Repeats 1-15 from within a particular well are flagged for manual or semi-automated review and data for all three wells for this individual sample is removed from further steps in the process. Specifically, this is done in an electronic manner for FAM in a Sample by comparing, by the one or more processors, a plurality of sample fluorescent intensity values against the dynamic value range and the static value range. If any well's FAM fluorescence intensity values, during the defined PCR cycles, falls outside the dynamic value range and/or the static value range, the sample is flagged for manual or semi-automated review. FAM fluorescence intensity values that statistically vary by 3.5 Standard Deviations from the average FAM fluorescence intensity values for Repeats 1-15 from of other FAM wells averages, during the specified cycles, on this plate may be flagged for manual or semi-automated review. Background—One or more processors identify any sample well that from Time 2464 and/or 55.0 (Temp) from Time 2464 and/or 55.0 (Temp) from Repeat 3-45 varies: Any Repeat Background fluorescence intensity value less than a determined static value range (e.g., 750) and/or any Repeat Background fluorescence intensity value greater than a determined static value range (e.g., 8,000), at any specified cycle, is flagged for manual or semi-automated review and data for all three wells for this individual sample and is removed from further steps in the process. Background fluorescence intensity values that statistically vary, at any specified cycle, by more or less than the established Background dynamic value range (e.g., 3.5 Standard Deviations) is flagged for manual or semi-automated review and data for all three well for this individual sample is removed from further steps in the process. Specifically, this is done in an electronic manner for Background in a Sample by comparing, by the one or more processors, a plurality of sample fluorescent intensity values against the dynamic value range and the static value range. If any well's Background values, during the specified cycles, falls outside the dynamic value range and/or the static value range, the sample may be flagged for manual or semi-automated review. MSE—Flag any well that from Time 2464 and 55.0 (Temp) from Repeat 3-15 varies: Any Repeat MSE value less than a determined static value (e.g., 750) and/or any Repeat MSE value greater than a determined static value (e.g., 8,000), at any cycle, is flagged for manual or semi-automated review and data for all three wells for this individual sample and is removed from further steps in the process. MSE values that statistically vary, at any cycle, by more or less than the established dynamic range (e.g., 3.5 Standard Deviations) is flagged for manual or semi-automated review and data for all three well for this individual sample is removed from further steps in the process. Specifically, this is done in an electronic manner for MSE in a Sample by comparing, by the one or more processors, a plurality of sample MSE values against the dynamic value range and the static value range. If any well's MSE values, during the defined PCR cycles, falls outside the dynamic value range and/or the static value range, the sample may be flagged for manual or semi-automated review.

If all the quality checks are passed LIMS 106 processors and systems moves on to the automated results determination. This involves processors and subsequent systems evaluating and predefined parameters associated with the Plate Controls, which may include No Template Controls (NTC), Positive control, and HSC (e.g., extraction control), respectively. Simultaneously, if the electronic systems analyses the results for the individual samples and determines the sample result. These electronic analysis parameters can be modified to conform with guidance directives issues by external agencies such as the Centers for Disease Control (CDC). The LIMS 106 processor and associated electronic systems determine the sample results automatically by electronically evaluating the Required Controls and the Samples of interest. The LIMS 106 determines the success of the instrumentation run by first electronically evaluating the if the fluorescence intensity data for a give fluorescent probe crossed Cycle Threshold for a particular target genetic sequence for both required Plate Controls as well as Samples. The point at which the fluorescence intensity for a given fluorescent probe crosses Threshold is calculated as a number and is known as the Cycle Threshold (Ct). The LIMS 106 processor and associated electronic systems electronically result based on the configurations below. Required Plate Controls and Controls Concordance: All control materials that are added to wells of the PCR have known results for each Control Type. All Control Types added to the plate should yield results that are concordant with the results of the known control materials. If the Control Type wells on the plate with the samples produce results that are non-concordant with the know results of the controls materials, then each sample associated with that plate will be invalidated electronically.

Examples of the Control Type includes the No Template Control (NTC)—consists of using nuclease-free water in the rRT-PCR reactions instead of RNA. The NTC reactions for all primer and probe sets should not exhibit fluorescence growth curves that cross the threshold line. If any of the NTC reactions exhibit a growth curve that crosses the cycle threshold, sample contamination may have occurred. LIMS 106 will invalidate the plate run for each sample on that particular plate, and potentially repeating the assay with strict adherence to the guidelines. 2019-nCoV Positive Control (nCoVPC)—consists of in vitro transcribed RNA. It will yield a positive result for N1, N2 primer/probe sets. Human Sample Control (HSC) (Extraction Control)—when run with the CDC SARS-CoV-2 rRT PCR Diagnostic Panel, the HSC is used as an RNA extraction procedural control to demonstrate successful recovery of RNA as well as extraction reagent integrity. The HSC control consists of noninfectious cultured human cell material. Purified nucleic acid form the HSC should yield a positive result with the RP primer/probe set, and negative results with all 2019-nCoV markers.

Results determination of samples is based on the cycle threshold value of each probe for a target genetic sequence in the sample compared to an established cycle threshold range. The samples cycle threshold values are inversely proportional to the amount of target nucleic acid in the sample. As seen in Table 1, the cycle threshold (Ct) value ranges are indicated for each target genetic sequence (i.e., N1, N2, and RP). Meaning, for example for the N1 target genetic sequence of the SARS-CoV-2 virus has an established the cycle threshold value range of <38.00 Ct (or equal to) is '+' or 'Positive' and any CT value >38.00 is '−' or 'Negative'.

When samples are run their cycle threshold values are electronically compared to the cycle threshold range as seen in Table 2. for of each target genetic sequence to determine the result. Specifically, determining a positive result for the presence of a target nucleic acid sequence in the sample is accomplished by comparing the sample cycle threshold to an established cycle threshold range, if less than the established cycle threshold range then the sample is determined to be a positive result for the presence of a target nucleic acid sequence in the sample. Likewise, determining a negative result for the presence of a target nucleic acid sequence in the sample is accomplished by comparing the sample cycle threshold to an established cycle threshold range, if less than the established cycle threshold range then the sample is determined to be a positive result for the presence of a target nucleic acid sequence in the sample.

RNase P (extraction control)—All clinical samples should exhibit fluorescence growth curves in the RNase P reaction that cross the threshold line within 35.00 cycles (<35.00 Ct), thus indicating the presence of human RNase P gene. If the RNase P assay does not produce a positive result for human clinical samples, interpret as follows: If the 2019-nCoV N1 and N2 are positive even in the absence of a positive RNase P, the result should be considered valid. It is possible, that some samples may fail to exhibit RNase P growth curves due to low cell numbers in the original clinical sample. A negative RNase P signal does not preclude the presence of 2019-nCoV virus RNA in a clinical sample. If all 2019-nCoV markers and RNase P are negative for the sample, the result should be considered invalid. If residual sample is available, repeat the extraction procedure and repeat the test. If all markers remain negative after re-test, report the results as invalid, collect a new sample.

TABLE 2

Expected Performance of Controls for SARS-CoV-2 Real-Time RT-PCR Diagnostic Panel: Cycle Threshold Ranges

| Control Type | External control name | Used to monitor | N1 | N2 | RP | Ct Value Ranges |
|---|---|---|---|---|---|---|
| Positive | nCoV PC | Substantial reagent failure including primer and probe integrity | + | + | − | <38.00 Ct is Positive Result. >38.00 Ct is Negative Result. |
| Negative | NTC | Reagent and/or environmental contamination | − | − | − | <45.0 Ct is Positive Result. >45.0 Ct is Negative Result. |
| Extraction | HSC | Failure in lysis and extraction procedure, potential contamination during extraction | − | − | + | <38.00 Ct is Positive Result. >38.00 Ct is Negative Result. |

Results interpretation: The result interpretation is an electronic process whereby each target genetic sequence result, either positive or negative, is used to create the 'Reportable Result'. Often, as seen in the SARS-CoV-2 assay, multiple target genetic sequences individual results (i.e., positive or negative) are compiled, evaluated collectively and used to produce the single 'Reportable Result'. Meaning, the interpretation results set (i.e., known results set) are combination of individuals positive and negative result combinations for each genetics target sequence. This combination of positive and negative results is compared to a known interpretation results set to derive the Reportable results. Specifically, one or more processors, matching the positive result and the negative result to a known control positive results and known control negative results, is demonstrated in Table 2. Meaning, the known positive control combination results for the SARS-CoV-2 assay is N1: '+'; N2: '+'; RP '+' therefore the SARS-CoV-2 positive control' results on the plate should be N1: '+'; N2: '+'; RP '+' and are matched to the known results set; likewise, for the negative control. If known control positive results and known control negative results do not match the sample is flagged for manual or semi-automated review.

TABLE 3

Reportable results
Result Set Interpretation

| N1 | N2 | RP | Reportable Results |
|---|---|---|---|
| + | + | + | Detected |
| + | + | − | Detected |
| − | + | + | Inconclusive |
| + | − | + | Inconclusive |
| − | − | + | Not Detected |
| − | − | − | Invalid Results |

For the SARS-CoV-2 assay a sample has a Reportable Result of 'Not Detected' if all N1 and N2 fluorescent intensity values do not cross the cycle threshold line within 38.00 cycles (<38.00 Ct) and the RNase P growth curve does cross the cycle threshold line within 38.00 cycles (<38.00 Ct). A sample is considered 'Detected' for SARS-CoV-2 if all SARS-CoV-2 markers N1 and N2 fluorescent intensity values cross the threshold line within 38.00 cycles (<38.00 Ct).

When the RP, N1 and N2 fluorescent intensity values do not cross the cycle threshold within 38.00 cycles (<38.00 Ct), the SARS-CoV-2 result is 'Invalid'. When the fluorescent intensity values for either N1 or N2, but not both, crosses the threshold line within 38.00 (<38.00 Ct) the result is 'Inconclusive'. In the preferred embodiment, comparing, by the one or more processors, the positive result and the negative result for the target nucleic acid sequence against a known interpretation result set to provide a clinically reportable result is accomplished in an automated manner. As seen in Table 4, one known interpretation results set for the SARS-CoV-2 assay is N1: '+'; N2: '+'; RP '+' therefore this sample's result combination yield a 'Detected' Reportable Result.

TABLE 4

LIMS 106 Automated SARS-CoV-2 rRT-PCR Diagnostic Assay
Result Interpretation and Reportable Results

| N1 | N2 | RP | Interpretation Know Result Set | Reportable Report | Action |
|---|---|---|---|---|---|
| + | + | + | +, +, + = Detected | DETECTED | Report Results Confirmation of Infection |
| + | + | − | +, +, − = Detected | DETECTED | Report Results Confirmation of Infection |

TABLE 4-continued

LIMS 106 Automated SARS-CoV-2 rRT-PCR Diagnostic Assay
Result Interpretation and Reportable Results

| N1 | N2 | RP | Interpretation Know Result Set | Reportable Report | Action |
|---|---|---|---|---|---|
| One of the two targets, N1 or N2, positive | | + | −, +, + = Inconclusive +, −, + = Inconclusive | INCONCLUSIVE | Report also contains an interpretive comment |
| − | − | + | −, −, + = Not Detected | NOT DETECTED | Report results. |
| − | +31 | − | −, −, − = Invalid Results | INVALID | Recommend specimen Recollection |

Now referring to FIG. 4, when the automated result for each of the samples are complete, the results are gathered by LIMS 106 and compiled. LIMS 106 then sends the test results to web server, which enters them in its order database. When the remote user initially created the order, the remote user transmitted the order information via relational database or web server, which saved the order information in its order database. This data includes the indicia of container in which the sample was inserted. Web server is configured to automatically retrieve this information from its order database and to incorporate this information into the test results. In the preferred embodiment, a LIMS 106 mechanism has been created to allow patients to receive test results immediately. The remote user's electronic information contains text and/or emails notification information that laboratory LIMS 106 processors and associated systems automatically and electronically act upon to text results and/or email results if desired at approximately the same time the results data is transmitted to the remote user's database.

From the foregoing, it will be observed that numerous modifications and variations can be affected without departing from the true spirit and scope of the novel concept of the present invention. It will be appreciated that the present disclosure is intended as an exemplification of the invention and is not intended to limit the invention to the specific embodiment illustrated. The disclosure is intended to cover by the appended claims all such modifications as fall within the scope of the claims.

For example, although databases have been identified for web server and LIMS 106, the data in these databases can be combined into fewer databases, including a single database, or can be further subdivided into a greater number of sub-databases. Furthermore, individual databases can be combined, and elements of each database can be moved from one database to another. Thus, a portion of any of the described databases can be incorporated into another database.

As another example, LIMS 106 is shown located at laboratory. LIMS 106 need not be located at laboratory, however, but can be located elsewhere and in communication with laboratory and with web server over a LAN, WAN, or the Internet.

Yet another example, the computers and servers described herein are each shown as software and data existing on a single computer. In an alternative embodiment, each may be comprised of multiple computers, with each computer performing a portion of the functions identified for the computers and servers.

Even further, while the description above relates to a particularly preferred application of biological testing, that of genotyping using Test Names and probes, the identical process can be used with other forms of biological testing, and even genotyping using profiles and primer sets. In such case, instead of having a Test Name database and associated probes, web server would have a profile database and manipulate Profiles (in place of the Test Names, above), and would have a primer set database and manipulate primer sets. Alternatively, animal Lines and Strains would have a primer and probe set database and manipulate primer and probe sets. Genotyping with Next Generation Sequencing (NGS), primer and index set would be in the database and manipulation of the primers and index set may be necessary for some applications. In the preferred embodiment illustrated above, the user at remote user computer interacts with a web server. Web communication over the Internet is preferred mode of placing an order. Dedicated programs and databases, however, can communicate the same information between remote user computer and another computer such as web server, that need not be configured to communicate with remote user computer as a web server, however. Instead, dedicated programs and databases operating on computer can communicate the same information back and forth between remote user computer and computer over the Internet, as seen in the relational database embodiment. If LIMS 106 is not located at test laboratory, additional computers at test laboratory can be configured to communicate over network with LIMS 106, to communicate information to LIMS 106 such as the identifiers or indicia on cooler boxes and sample containers shipped to testing lab from the remote user and containing her order.

In the preferred embodiment, all the web pages are described as being generated by "web server". In an alternative embodiment, web server may be a plurality of individual web servers each providing a different web page. In another alternative embodiment, these individual web servers may be disposed at different locations, and communication between the remote user computer and web server may include transmissions from remote user computer to two or more different physical computers located at two or more different locations, each one of which can perform any one or more of the functions described above as being performed by web server.

From the foregoing, it will be observed that numerous modifications and variations can be affected without departing from the true spirit and scope of the novel concept of the present invention. It will be appreciated that the present disclosure is intended as an exemplification of the invention and is not intended to limit the invention to the specific embodiment illustrated. The disclosure is intended to cover by the appended claims all such modifications as fall within the scope of the claims.

What is claimed is:

1. A computer implemented system to provide a reportable result to a remote client for the presence of a target nucleic acid sequence comprising:
 a plurality of samples, wherein each sample of the plurality of samples is disposed in a sample well, each sample well provided with a portion of the sample and a plurality of primers for amplifying the target nucleic acid sequence;
 an automated laboratory instrumentation configured to perform respective functions, wherein said respective functions comprise:
 obtaining a fluorescent intensity value for a polymerase chain reaction amplification cycle from each sample well;
 an electronic interface configured to transmit a plurality of patient specific information associated with each sample from the remote client to a laboratory information management system computer, said laboratory information management system computer comprised of a computer system having a microprocessor and a non-transitory computer-readable storage medium coupled to said microprocessor, wherein said non-transitory computer-readable storage medium is encoded with computer-readable instructions;
 wherein when said computer-readable instructions are executed, said microprocessor performs the respective functions, wherein said functions comprises:
 electronically generating a fluorescent intensity value range based on the fluorescent intensity value for the polymerase chain reaction amplification cycle for each sample wells for the sample and for a control;
 electronically generating a dynamic value range based on the fluorescent intensity for polymerase chain reaction amplification cycle from each of the plurality of sample wells for the sample and the control;
 electronically generating a static value range based on the fluorescent intensity for polymerase chain reaction amplification cycle from each of the plurality of sample wells for the sample and the control;
 flagging the sample for manual review if the fluorescent intensity is outside the dynamic value range and the static value range; wherein the step of flagging the samples for manual review removes a particular fluorescent intensity value of a sample well from the step of: comparing, by the one or more processors, the plurality of sample fluorescent intensity values against the fluorescent intensity value range;
 comparing, by the one or more processors, the plurality of sample fluorescent intensity values against the fluorescent intensity value range;
 evaluating a sample cycle threshold value for each well of the plurality of sample wells against an established cycle threshold range;
 determining a positive result and a negative result for the presence of a target nucleic acid sequence in the sample by comparing the sample cycle threshold value to an established cycle threshold range; and
 comparing, by the one or more processors, the positive result, and the negative result for the target nucleic acid sequence against a known interpretation result set to provide a reportable result, wherein the electronic interface is configured to transmit the reportable result to the remote client.

2. The system of claim 1, further comprising an electronic system comprised of a computer configured to electronically communicate with the remote client.

3. The system of claim 1, wherein the one or more processors are configured to automatically provide an electronic text message to a user of the reportable result.

4. The system of claim 1, wherein the electronic system is configured to provide a display of a web-based user interface configured to receive from the user an input of a request for the assay wherein the input is comprised of patient information from scanning barcodes on a back of the patient's driver license.

5. The system of claim 1, wherein the target nucleic acid sequence is SARS-CoV-2 or a variant thereof.

6. The system of claim 1, wherein the target nucleic acid sequence is a human gene.

7. The system of claim 1, wherein the electronic interface is configured to electronically populate a plurality of sample specific information through an electronic interface;

electronically transmitting over the Internet, a first plurality of patient information associated with a first biological sample to the laboratory information management system computer processor configured to receive electronic order information for a biological tests.

8. The system of claim 1, comprising a physical container containing the sample received from a user, wherein the physical container includes sample specific data comprised of a machine-readable code, the method further comprising the step of tracking the sample electronically by scanning the machine-readable code.

9. The system of claim 1, wherein the laboratory information management system computer, further provides: electronically matching a control type positive result and a control type negative result for the target genetic sequence on a sample plate to a known plate control result for the target genetic sequence, and then invalidating, by one or more electronic processors, the sample on the sample plate where the plate control results are discordant with the known plate control result.

10. A non-transitory computer-readable memory medium, on which computer-executable instructions are stored which, when executed on a data-processing system, prompt the data-processing system to carry out the steps of a method, of validating a plurality of fluorescent intensity values for a polymerase chain reaction amplification cycle from each of a plurality of wells for a sample and for a control, the validation method comprising:

electronically generating a dynamic value range based on the plurality of fluorescent intensity values for a sample and for a control;

electronically generating a static value range based on the plurality of fluorescent intensity values for the sample and for the control;

comparing, by the one or more processors, the plurality of sample fluorescent intensity values against the dynamic value range and the static value range;

flagging the sample for manual review if the fluorescent intensity is outside the dynamic value range and the static value range; wherein the step of flagging the samples for manual review removes a particular fluorescent intensity value of a sample well from the step of: evaluating a sample cycle threshold value for each well of the plurality of sample wells against an established cycle threshold range;

evaluating a sample cycle threshold value for each well of the plurality of sample wells against an established cycle threshold range;

determining by the one or more processors, a positive result for the presence of a target nucleic acid sequence in the sample by comparing the sample cycle threshold value to an established cycle threshold range, if less than the established cycle threshold range then the sample is determined to be a positive result for the presence of the target nucleic acid sequence in the sample;

determining by the one or more processors, a negative result for the presence of the target nucleic acid sequence in the sample by comparing the sample cycle threshold value to an established cycle threshold range, if greater than the established cycle threshold range then the sample is determined to be a negative result for the presence of the target nucleic acid sequence in the sample;

matching by the one or more processors, the positive result and the negative result to a and known control negative result; and comparing, by the one or more processors, the positive result, and the negative result for the target nucleic acid sequence against a known interpretation result set to provide a validated test result.

11. The method of claim 10, wherein the target nucleic acid sequence is selected from the group consisting of: SARS-CoV-2 or a variant thereof and a human gene.

* * * * *